(12) United States Patent
Chun

(10) Patent No.: US 9,538,902 B2
(45) Date of Patent: Jan. 10, 2017

(54) IMAGE PROCESSING DEVICE AND METHOD FOR OPERATING ENDOSCOPE SYSTEM

(71) Applicant: FUJIFILM Corporation, Tokyo (JP)

(72) Inventor: Minkyung Chun, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/866,301

(22) Filed: Sep. 25, 2015

(65) Prior Publication Data

US 2016/0007830 A1    Jan. 14, 2016

Related U.S. Application Data

(63) Continuation of application No. PCT/JP2014/057714, filed on Mar. 20, 2014.

(30) Foreign Application Priority Data

Mar. 27, 2013  (JP) ................................. 2013-066283
Sep. 27, 2013  (JP) ................................. 2013-201275

(51) Int. Cl.
*G06T 7/00* (2006.01)
*A61B 1/00* (2006.01)
(Continued)

(52) U.S. Cl.
CPC ....... *A61B 1/00009* (2013.01); *A61B 1/00045* (2013.01); *A61B 1/0638* (2013.01);
(Continued)

(58) Field of Classification Search
CPC ................... G06T 7/0012; G06T 7/408; G06T 2207/10068; A61B 1/00009; A61B 5/1032
(Continued)

(56) References Cited

U.S. PATENT DOCUMENTS

2006/0006428 A1* 1/2006 Song ................. H01L 27/14603
257/232
2007/0153542 A1* 7/2007 Gono ................... A61B 1/0638
362/574
(Continued)

FOREIGN PATENT DOCUMENTS

JP    3228627 B2    11/2001

OTHER PUBLICATIONS

International Search Report, issued in PCT/JP2014/057714, dated, Jun. 24, 2014.
(Continued)

*Primary Examiner* — Yubin Hung

(74) *Attorney, Agent, or Firm* — Birch, Stewart, Kolasch & Birch, LLP

(57) ABSTRACT

A first signal ratio (–log(B/G)) between a B image signal and a G image signal is calculated. A second signal ratio (–log (G/R)) between the G image signal and an R image signal is calculated. A difference between first and second signal ratios in a first area and first and second signal ratios in a specific area is increased to enhance a color difference between normal mucosa and an abnormal region (an atrophic mucosal region and a deep blood vessel region). The color difference between the normal mucosa and the abnormal region in a case where at least one of the RGB image signals is a narrowband image signal is greater than the color difference in a case where all of the RGB image signals are broadband image signals.

12 Claims, 20 Drawing Sheets

(51) Int. Cl.
*A61B 5/103* (2006.01)
*A61B 1/06* (2006.01)
*G06T 7/40* (2006.01)
*A61B 1/273* (2006.01)

(52) U.S. Cl.
CPC .......... *A61B 1/0653* (2013.01); *A61B 5/1032* (2013.01); *G06T 7/0012* (2013.01); *G06T 7/408* (2013.01); *A61B 1/063* (2013.01); *A61B 1/2736* (2013.01); *G06T 2207/10024* (2013.01); *G06T 2207/10068* (2013.01); *G06T 2207/30092* (2013.01)

(58) Field of Classification Search
USPC .................................................. 382/128, 254
See application file for complete search history.

(56) References Cited

U.S. PATENT DOCUMENTS

| | | | | |
|---|---|---|---|---|
| 2007/0165284 | A1* | 7/2007 | Li | H04N 1/409 358/3.27 |
| 2010/0092055 | A1* | 4/2010 | Matsuda | A61B 1/00009 382/128 |
| 2010/0119110 | A1* | 5/2010 | Kanda | A61B 1/00009 382/103 |
| 2011/0077462 | A1* | 3/2011 | Saitou | A61B 1/0638 600/109 |
| 2011/0237883 | A1* | 9/2011 | Chun | A61B 1/0638 600/109 |
| 2012/0127293 | A1* | 5/2012 | Yamazaki | A61B 1/00009 348/71 |

OTHER PUBLICATIONS

Written Opinion of the International Searching Authority, issued in PCT/JP2014/057714, dated, Jun. 24, 2014.
Chinese Office Action and Chinese Search Report, issued Apr. 5, 2016, for Chinese Application No. 201480018499.7.
Extended European Search Report, issued Jun. 1, 2016, for European Application No. 14772767.1.
Partial English Translation of Chinese Office Action, dated Apr. 5, 2016, for Chinese Application No. 201480018499.7.

\* cited by examiner (A)

(B)

(A)

(B)

IMAGE PROCESSING DEVICE AND METHOD FOR OPERATING ENDOSCOPE SYSTEM

CROSS-REFERENCE TO RELATED APPLICATIONS

This application is a Continuation of PCT International Application No. PCT/JP2014/057714 filed on Mar. 20, 2014, which claims priority under 35 U.S.C. §119(a) to Japanese Patent Application No. 2013-066283, filed Mar. 27, 2013 and Japanese Patent Application No. 2013-201275, filed Sep. 27, 2013. Each of the above application(s) is hereby expressly incorporated by reference, in its entirety, into the present application.

BACKGROUND OF THE INVENTION

1. Field of the invention

The present invention relates to an image processing device for processing images used for diagnosing atrophic gastritis and a method for operating an endoscope system.

2. Description Related to the Prior Art

Diagnoses using endoscope systems have been widely performed in medical fields. The endoscope system comprises a light source device, an electronic endoscope, and a processor device. Due to high resolution achieved by a high-definition imaging system such as an imaging element, which is to be incorporated in the endoscope, with high sensibility and a high number of pixels, recent models of the endoscope systems display high resolution images that surpass the current image quality. Owing to this, fine blood vessels and a small lesion in mucosa displayed look extremely real.

Such high-definition imaging clarifies the shape and the size of a lesion, facilitating the detection of the lesion. However, a doctor finds a lesion based not only on the shape and the size of the lesion but also on a slight difference in color between portions of mucosa. For example, a slightly reddish area that is slightly different in color from the mucosa is detected as a lesion in its early stage. The slightly reddish area may be overlooked only by increasing the resolution with the use of the high-definition imaging.

In Japanese Patent No. 3228627, a color enhancement process is performed to enhance the redness of a reddish area and the whiteness of a white area in an image to prominently display a border between a normal portion and a lesion. The color enhancement process enables finding a lesion which cannot be detected only by using the high-definition imaging.

In recent years, a stomach lesion such as stomach cancer has been detected based on a state of atrophic gastritis. The relationship between the atrophic gastritis and the stomach lesion, which will be described below, is used for the detection. As illustrated in a part (A) of FIG. 30, a surface mucosal layer of normal gastric mucosal structure has certain thickness, so that the mucosal layer absorbs or reflects most of the light. For this reason, the blood vessels in the normal submucosal layer are hardly observed in an endoscopic image as illustrated in a part (B) of FIG. 30.

As illustrated in a part (A) of FIG. 31, in the case of gastric mucosal structure in an advanced stage of the atrophic gastritis, the mucosal layer is thin due to decrease in gastric glandular cells. Changes in internal structure of the gastric mucosa with the progress of the atrophic gastritis exhibit the following features (A) and (B) in an endoscopic image.

(A) The whitish color of muscularis mucosae is seen through the atrophic mucosa, so that the atrophic mucosal portion shows fading of color as compared with the color of the normal portion.

(B) The blood vessels in the submucosal layer are seen through the mucosal layer in the atrophic mucosal portion as the thickness of the mucosal layer decreases with the progress of the atrophy (see a part (B) of FIG. 31).

In diagnosing a gastric lesion based on the atrophic gastritis, the above-described two features (A) and (B) are used for determining staging of atrophy and a border between the normal portion and the portion with the gastritis.

In a case where the atrophy is in its advanced stage (for example, in a case where the atrophy is included in the group C or the group D in the ABC screening), the above-described features (A) and (B) are clearly observed in the endoscopic image. However, in a case where the atrophy is in an intermediate stage (for example, in a case where the atrophy is included in the group B or the group C in the ABC screening), there is little difference between the atrophic portion and the normal portion in the endoscopic image, so that it may be difficult to determine the staging of atrophy and the border between the normal portion and the portion with the gastritis. It is required to display the two features (A) and (B) clearly in the endoscopic image to clarify the border between the normal portion and the portion with the gastritis.

The method described in the Japanese Patent No. 3228627 may be applied to achieve the above. However, the method described in the Japanese Patent No. 3228627 enhances only the redness of a reddish area in an image and cannot enhance the changes in color of mucosa with the progress of the atrophy of the stomach and cannot enhance and display the blood vessels that are located beneath the mucosa and seen through the mucosa as the atrophy progresses.

SUMMARY OF THE INVENTION

An object of the present invention is to provide an image processing device that enhances changes in color of mucosa or the like in an image due to atrophy of stomach caused by atrophic gastritis and a method for operating an endoscope system.

In order to achieve the above and other objects, an aspect of the present invention provides an image processing device comprising an image signal inputting unit, a signal ratio calculator, a color difference enhancer, and a display unit. The image signal inputting unit inputs image signals of three colors including at least one narrowband image signal. The signal ratio calculator calculates a first signal ratio between the image signals of predetermined two colors and a second signal ratio between the image signals of two colors different from the first signal ratio, based on the image signals of three colors. The color difference enhancer performs an expansion process for expanding a difference between first and second signal ratios in a first area and first and second signal ratios in a specific area different from the first area. The display unit displays an image in which a color difference between normal mucosa and an abnormal region on an object of interest is enhanced based on the first and second signal ratios subjected to the expansion process. The color difference is displayed greater than a color difference in a case where all of the image signals of three colors are broadband image signals.

It is preferred that a difference in reflection density between the normal mucosa and the abnormal region is greater than a difference in reflection density in the case where all of the image signals of three colors are the broadband image signals. It is preferred that the difference in reflection density between the normal mucosa and the abnormal region increases as wavelengths corresponding to the narrowband image signal become shorter.

It is preferred that the abnormal region includes at least one of mucosa showing fading of color including atrophic mucosa, a blood vessel region beneath the mucosa showing fading of color, a brownish area (BA) region, and a mild redness region. It is preferred that the narrowband image signal is obtained by imaging the object irradiated with narrowband light that is highly absorbed by blood. It is preferred that the narrowband image signal is a blue narrowband image signal obtained by imaging the object irradiated with blue narrowband light that is highly absorbed by the blood or a green narrowband image signal obtained by imaging the object irradiated with green narrowband light that is highly absorbed by the blood.

It is preferred that the expansion process is a process for expanding a radial coordinate difference or an angular coordinate difference between the first and second signal ratios in the first area and the first and second signal ratios in the specific area. It is preferred that the expansion process expands the difference between the first and second signal ratios in the first area and the first and second signal ratios in the specific area while the first and second signal ratios in the first area are maintained unchanged, and the display unit displays an image in which a color of the normal mucosa is maintained unchanged. It is preferred that the image processing device further comprises an average value calculator for calculating an average value of the first and second signal ratios in the first area. It is preferred that the color difference enhancer expands a difference between the average value and the first and second signal ratios in the specific area. It is preferred that a suppression process for reducing the enhancement of the color difference is performed in a high luminance area or a low luminance area in the first area and the specific area. It is preferred that the first signal ratio is a B/G ratio between a B image signal, being the narrowband image signal, and a G image signal, and the second signal ratio is a G/R ratio between the G image signal and an R image signal.

An aspect of the present invention provides a method for operating an endoscope system comprising an image signal input step, a signal ratio calculation step, a color difference enhancement step, and a display step. In the image signal input step, an image signal inputting unit inputs image signals of three colors including at least one narrowband image signal. In the signal ratio calculation step, a signal ratio calculator calculates a first signal ratio between the image signals of predetermined two colors and a second signal ratio between the image signals of two colors different from the first signal ratio, based on the image signals of three colors. In the color difference enhancement step, a color difference enhancer performs an expansion process. The expansion process expands a difference between first and second signal ratios in a first area and first and second signal ratios in a specific area different from the first area. In the display step, a display unit displays an image in which a color difference between normal mucosa and an abnormal region on an object of interest is enhanced based on the first and second signal ratios subjected to the expansion process. The color difference is displayed greater than a color difference in a case where all of the image signals of three colors are broadband image signals.

According to an aspect of the present invention, the changes in color of the mucosa or the like in the image due to the atrophy of stomach caused by the atrophic gastritis are enhanced.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

Figure 30:
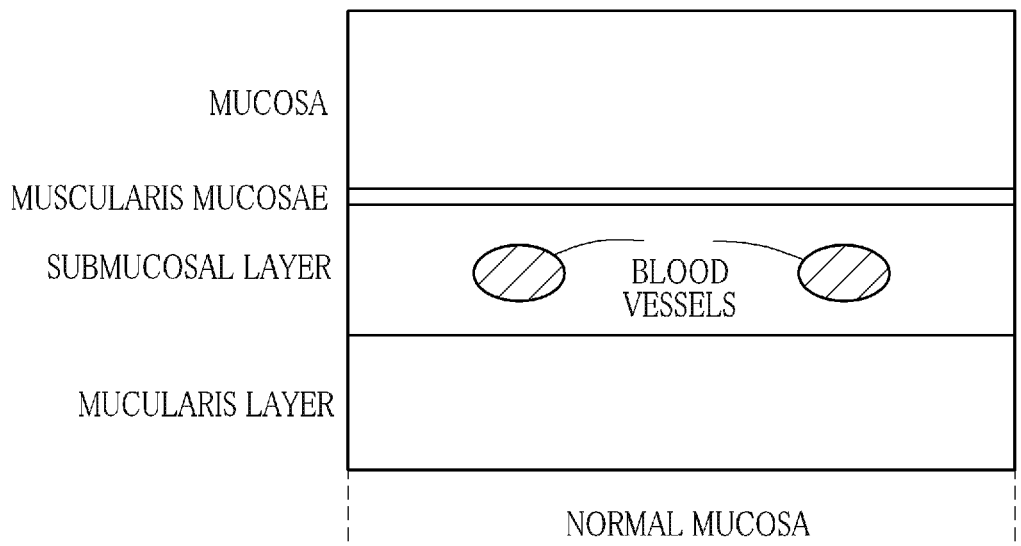
Figure 30:
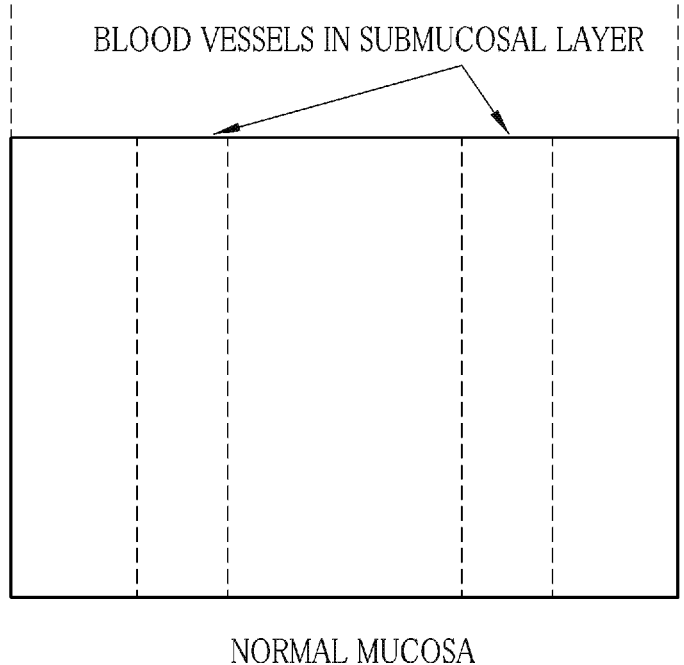
Figure 31:
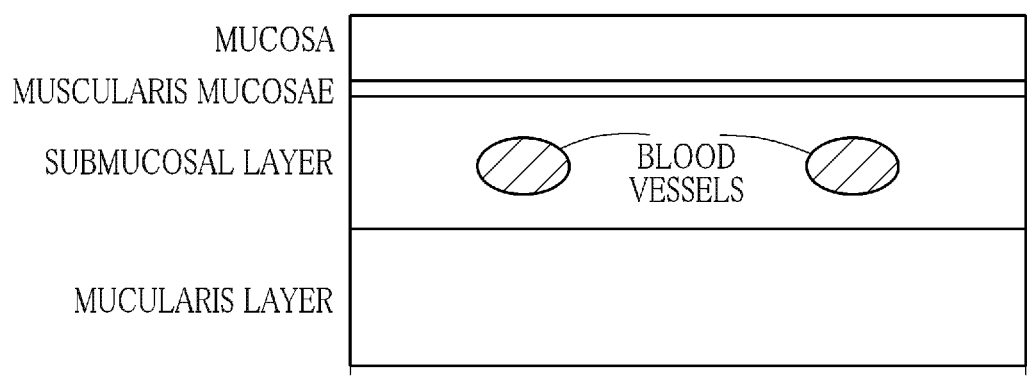
Figure 31:
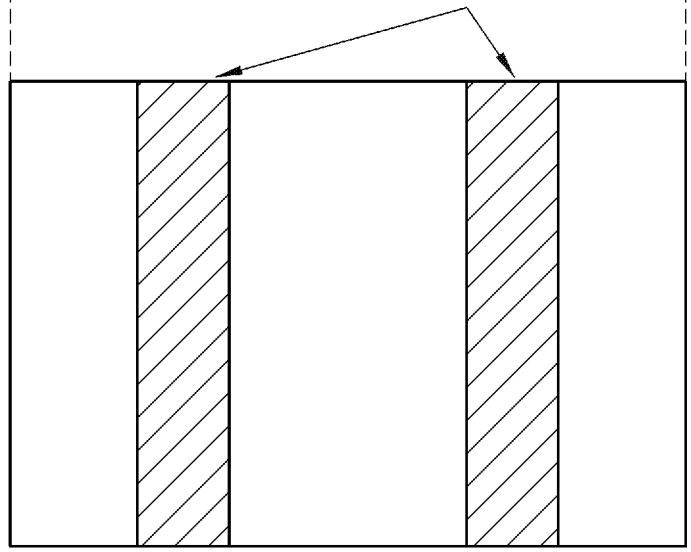

A part (A) of FIG. 30 is a cross-sectional view of a mucosal structure of normal mucosa and a part (B) of FIG. 30 is a plan view of the normal mucosa viewed from a surface layer side;

A part (A) of FIG. 31 is a cross-sectional view of a mucosal structure with the atrophic gastritis in which the thickness of gastric mucosal layer is reduced due to decrease in glandular cells of stomach or substitution of intestinal tissue or fibrous tissue for stomach tissue, and a part (B) of FIG. 31 is a plan view of mucosa with the atrophic gastritis viewed from the surface layer side.

DESCRIPTION OF THE PREFERRED EMBODIMENTS

First Embodiment

Figure 1:
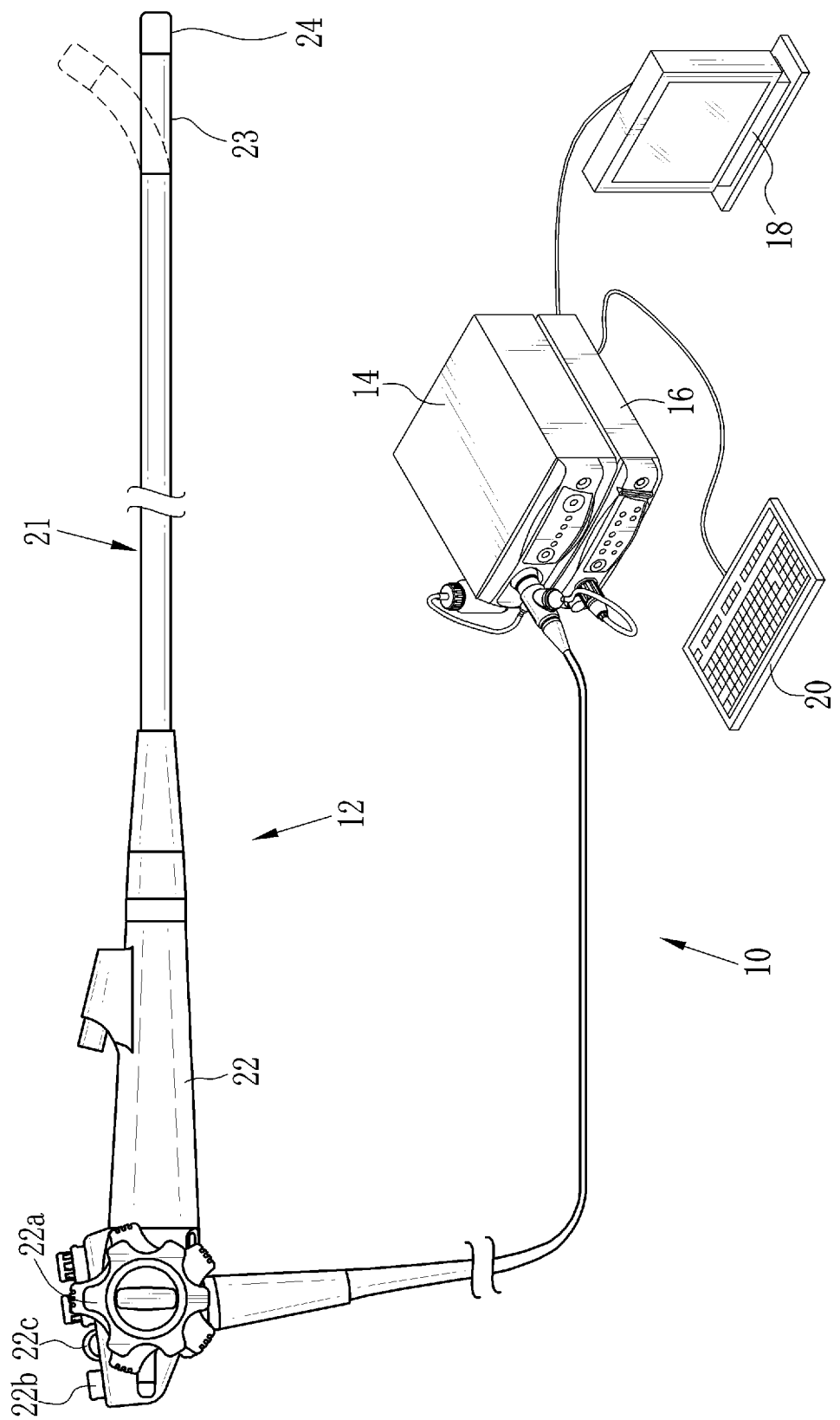
FIG. 1 is an external view of an endoscope system.

In FIG. 1, an endoscope system 10 according to a first embodiment comprises an endoscope 12, a light source device 14, a processor device 16, a monitor 18, and a console 20. The endoscope 12 is connected optically to the light source device 14 and electrically to the processor device 16. The endoscope 12 comprises an insertion section 21 to be inserted into a body cavity, a control handle unit 22 provided at the proximal end of the insertion section 21, a flexible portion 23, and a distal portion 24. The flexible portion 23 and the distal portion 24 are provided on the distal side of the insertion section 21. The flexible portion 23 is bent by operating an angle knob 22a of the control handle unit 22. The distal portion 24 is directed to a desired direction by bending the flexible portion 23.

The control handle unit 22 is provided with the angle knob 22a, a mode switch (SW) 22b, and a zoom operating section 22c. The mode SW 22b is operated to switch between two observation modes: a normal observation mode and a special observation mode. In the normal observation mode, a body cavity is irradiated with white light. In the special observation mode, the body cavity is irradiated with special light of a bluish color, and the changes in colors of mucosa and blood vessels seen through the mucosa that may occur due to the atrophy of stomach caused by atrophic gastritis are enhanced. The zoom operating section 22c drives a zooming lens 47 (see FIG. 2), which is provided in the endoscope 12, to magnify an object. Note that in the special observation mode, the white light may be used instead of the special light.

The processor device 16 is electrically connected to the monitor 18 and the console 20. The monitor 18 outputs and displays image information and the like. The console 20 functions as a UI (user interface), which receives input operation such as setting a function. Note that an external storage unit (not shown) for recording the image information and the like may be connected to the processor device 16.

Figure 2:
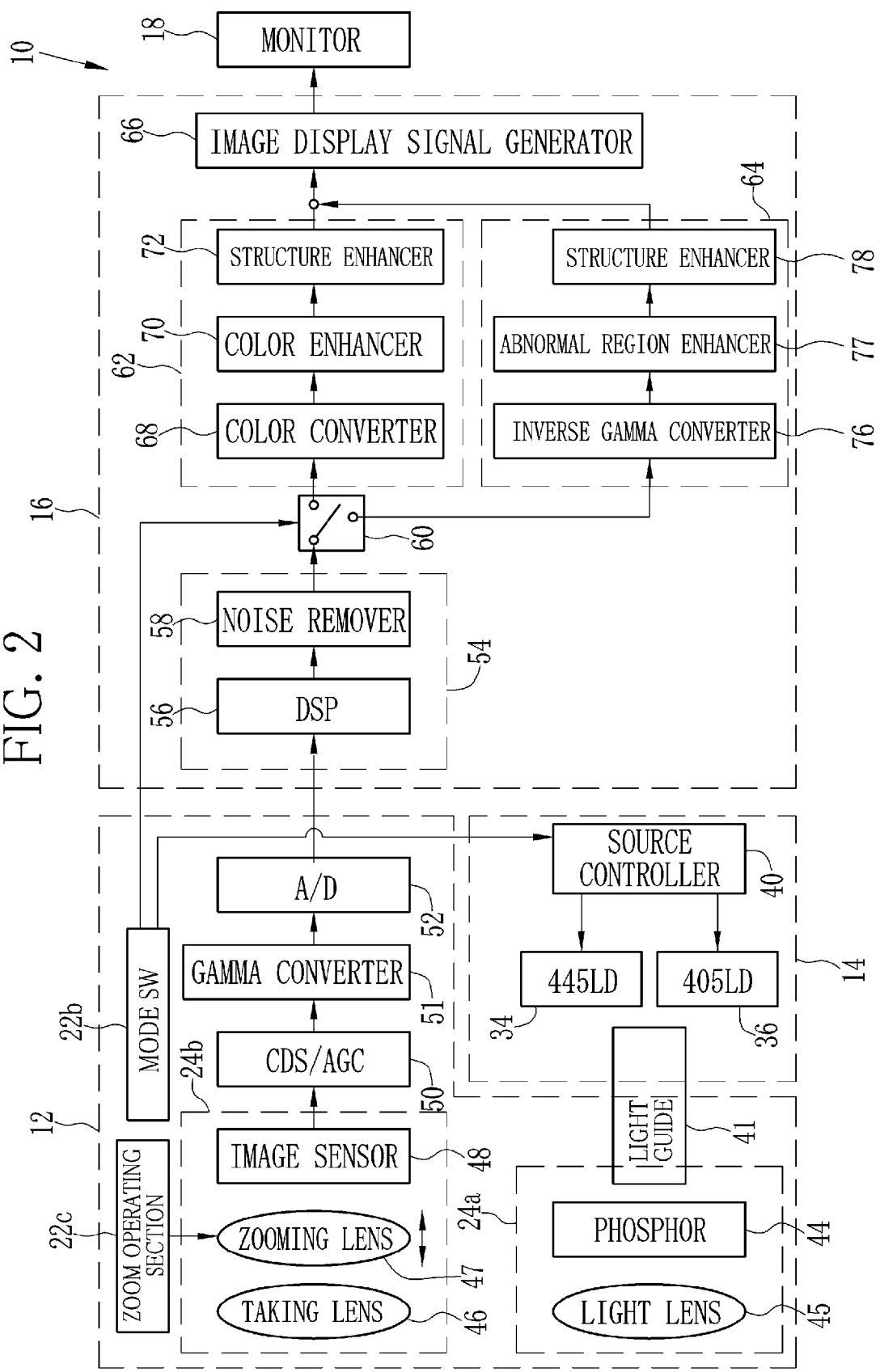
FIG. 2 is a block diagram illustrating functions of the endoscope of a first embodiment.

As illustrated in FIG. 2, the light source device 14 comprises a blue laser (445LD) 34 and a blue violet laser (405LD) 36, being the light sources. The blue laser (445LD) 34 emits blue laser beams having the center wavelength 445 nm. The blue violet laser (405LD) 36 emits blue violet laser beams having the center wavelength 405 nm. The light emissions from the semiconductor light emitting elements of each of the lasers 34 and 36 are controlled independently by a source controller 40. A light quantity ratio between the light from the blue laser 34 and the light from the blue violet laser 36 is changed as desired. In the normal observation mode, the source controller 40 actuates the blue laser 34, mostly, and controls the blue laser 34 to allow slight emission of the blue violet laser beams. Note that the blue violet laser 36 may be actuated in the normal observation mode. In this case, it is preferred to maintain the emission intensity of the blue violet laser 36 at a low level. In the special observation mode, both of the blue laser 34 and the blue violet laser 36 are actuated. The light emission ratio is controlled such that the light emission ratio of the blue laser beams is greater than that of the blue violet laser beams. Note that it is preferred that the full width at half maximum of the blue laser beams or the blue-violet laser beams is in the order of ±10 nm. Broad-area type InGaN-based laser diodes, InGaNAs-based laser diodes, or GaNAs-based laser diodes may be used as the blue laser 34 and the blue-violet laser 36. A light emitting element such as a light emitting diode may be used as the light source.

The laser beams from each of the lasers 34 and 36 enter a light guide (LG) 41 through optical members such as a condenser lens, an optical fiber, a combiner, and the like (all not shown). The light guide 41 is incorporated in the light source device 14, the endoscope 12, and a universal cord (a cord for connecting the endoscope 12 to the light source device, not shown). The blue laser beams having the center wavelength of 445 nm or the blue violet laser beams having the center wavelength of 405 nm are transmitted to the distal portion 24 of the endoscope 12 through the light guide 41. Note that a multimode fiber may be used as the light guide 41. For example, a small-diameter fiber cable with the core diameter 105 μm, the clad diameter 125 μm, and the outer diameter φ 0.3 to 0.5 mm (including a protection layer, being a jacket) may be used.

The distal portion 24 of the endoscope 12 comprises an illumination optical system 24a and an imaging optical system 2b. The illumination optical system 24a comprises phosphor 44 and a light lens 45. The blue laser beams having the center wavelength 445 nm or the blue violet laser beams having the center wavelength 405 nm, which are transmitted through the light guide 41, are incident on the phosphor 44. The phosphor 44 irradiated with the blue laser beams emits fluorescence. A part of the blue laser beams pass through the phosphor 44. The blue-violet laser beams pass through the phosphor 44 without exciting the phosphor 44. The light emanating from the phosphor 44 is applied to the object through the light lens 45.

Figure 3:
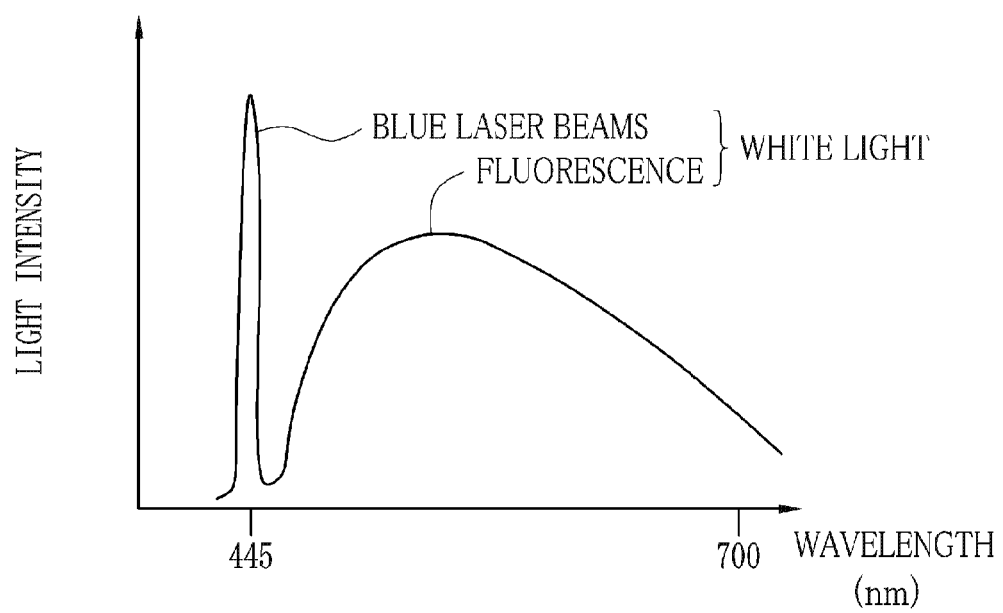
FIG. 3 is a graph illustrating spectral intensity of white light.
Figure 4:
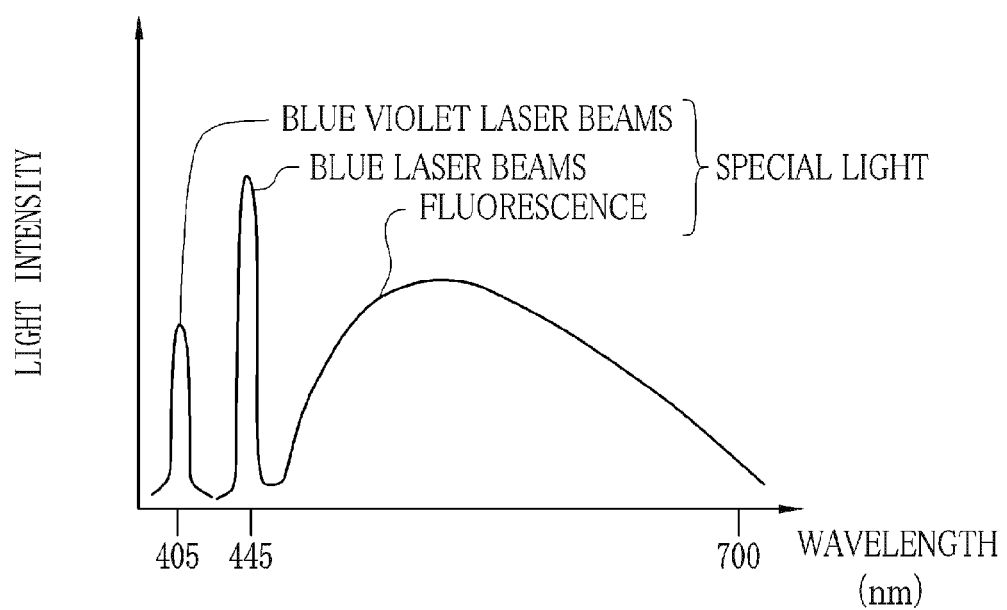
FIG. 4 is a graph illustrating spectral intensity of special light.

Here, in the normal observation mode, the blue laser beams are mostly incident on the phosphor 44, so that the white light, being the combination of the blue laser beams and the fluorescence from the phosphor 44 excited by the blue laser beams as illustrated in FIG. 3, is applied to the body cavity. In the special observation mode, both the blue-violet laser beams and the blue laser beams are incident on the phosphor 44, so that the special light, being the combination of the blue-violet laser beams, the blue laser beams, and the fluorescence from the phosphor 44 excited by the blue laser beams as illustrated in FIG. 4, is applied to the body cavity. In the special observation mode, the special light is broadband light that includes a high amount of blue component and the wavelength of which covers substantially the entire visible range because the special light includes the blue violet laser beams in addition to the blue laser beams, in which the light emission intensity of the blue component is high.

Note that it is preferred to use the phosphor 44 containing two or more types of phosphor (e.g. YAG-based phosphor, BAM(BaMgAl$_{10}$O$_{17}$), or the like) that absorb a part of the blue laser beams and emit light of green to yellow colors. In the case where the semiconductor light emitting elements are used as the excitation light sources for the phosphor 44 as described in this example, the high-intensity white light is provided with high light-emission efficiency, the intensity of the white light is controlled easily, and the variations in the color temperature and chromaticity of the white light are maintained at a low level.

As illustrated in FIG. 2, the imaging optical system 24b of the endoscope 12 has a taking lens 46, the zooming lens 47, and an image sensor 48. The light reflected from the object is incident on the image sensor 48 through the taking lens 46 and the zooming lens 47. Thereby a reflection image of the object is formed on the image sensor 48. Operating the zoom operating section 22c moves the zooming lens 47 between the telephoto end and the wide angle. The size of the reflection image of the object is reduced when the zooming lens 47 is moved to the wide angle end side. The size of the reflection image of the object is magnified when the zooming lens is moved to the telephoto end side.

The image sensor 48 is a color image sensor, which captures the reflection image of the object and outputs image signals. Note that it is preferred that the image sensor 48 is a CCD (Charge Coupled Device) image sensor, a CMOS (Complementary Metal-Oxide Semiconductor) image sensor, or the like. The image sensor used in the present invention is an RGB image sensor having RGB channels (ch) and provided with RGB color filters on an imaging plane. Photoelectric conversion is performed for each channel. Thereby an R image signal is outputted from an R pixel provided with an R (red) color filter. A G image signal is outputted from a G pixel provided with a G (green) color filter. A B image signal is outputted from a B pixel provided with a B (blue) color filter.

Note that the image sensor 48 may be an image sensor comprising CMYG filters (C: cyan, M: magenta, Y: yellow, and G: green) on the imaging plane. In the case where the image sensor with the CMYG filters is used, CMYG image signals of four colors are converted into the RGB image signals of three colors. In this case, it is necessary that one of the endoscope 12, the light source device 14, and the processor device 16 comprises a color conversion means for converting the CMYG image signals of four colors into the RGB image signals of three colors.

The image signal outputted from the image sensor 48 is transmitted to a CDS/AGC circuit 50. The CDS/AGC circuit 50 performs correlated double sampling (CDS) and automatic gain control (AGC) on the image signal that is an analog signal. A gamma converter 51 performs gamma conversion on the image signal that has passed through the CDS/AGC circuit 50. Thereby an image signal having a tone suitable for an output device (e.g. the monitor 18) is generated. After the gamma conversion, an A/D converter 52 converts the image signal into a digital image signal. The A/D converted digital image signal is inputted to the processor device 16.

The processor device 16 comprises a receiver 54, an image processing selector 60, a normal light image processing unit 62, a special light image processing unit 64, and an image display signal generator 66. The receiver 54 receives digital image signals from the endoscope 12. The receiver 54 comprises a DSP (Digital Signal Processor) 56 and a noise remover 58. The DSP 56 performs gamma correction and color correction on the digital image signals. The noise remover 58 removes noise from the digital image signals that have been subjected to the gamma correction and the like performed by the DSP 56, through a noise removing process (for example, moving average method or median filter method). The digital image signals from which the noise has been removed are transmitted to the image processing selector 60. Note that the "image signal inputting unit" of the present invention corresponds to the configuration that includes the receiver 54, for example.

In a case where the mode is set to the normal observation mode with the use of the mode SW 22b, the image processing selector 60 transmits the digital image signals to the normal light image processing unit 62. In a case where the mode is set to the special observation mode, the image processing selector 60 transmits the digital image signals to the special light image processing unit 64.

The normal light image processing unit 62 comprises a color converter 68, a color enhancer 70, and a structure enhancer 72. The color converter 68 assigns the inputted digital image signals of three channels (RGB) to R image data, G image data, B image data, respectively. The RGB image data is converted into color-converted RGB image data by a color conversion process such as 3×3 matrix processing, a tone conversion process, or a three-dimensional LUT process.

The color enhancer 70 performs various types of color enhancement processes on the color-converted RGB image data. The structure enhancer 72 performs a structure enhancement process (spatial frequency enhancement or the like) on the color-enhanced RGB image data. The RGB image data that has been subjected to the structure enhancement process performed by the structure enhancer 72 is inputted as the normal light image from the normal light image processing unit 62 to the image display signal generator 66.

The special light image processing unit 64 has an inverse gamma converter 76, an abnormal region enhancer 77, and a structure enhancer 78. The inverse gamma converter 76 performs inverse gamma conversion on the digital image signals of three channels (RGB) inputted. Since the RGB image signals after the inverse gamma conversion are reflectance-linear RGB signals, which change linearly relative to the reflectance from the object, the reflectance-linear RGB signals contain a high amount of various types of biological information (in this embodiment, information about the atrophy of stomach such as changes in color of the stomach caused by the atrophic gastritis) of the object.

Based on the reflectance-linear RGB image signals, the abnormal region enhancer 77 performs a color difference enhancement process for enhancing a difference in color between a normal mucosal region and an abnormal region, which may contain a lesion such as stomach cancer. The details of the abnormal region enhancer 77 will be described below. The structure enhancer 78 performs the structure enhancement process such as the spatial frequency enhancement on the RGB image data that has been subjected to the color difference enhancement process. The RGB image data that has been subjected to the structure enhancement process performed by the structure enhancer 78 is inputted as the special light image from the special light image processing unit 64 to the image display signal generator 66.

The image display signal generator 66 converts the normal light image, which is inputted from the normal light image processing unit 62, or the special light image, which is inputted from the special light image processing unit 64, into a display image signal, which is to be displayed as a displayable image on the monitor 18. Based on the display image signal after the conversion, the monitor 18 displays the normal light image or the special light image.

Figure 5:
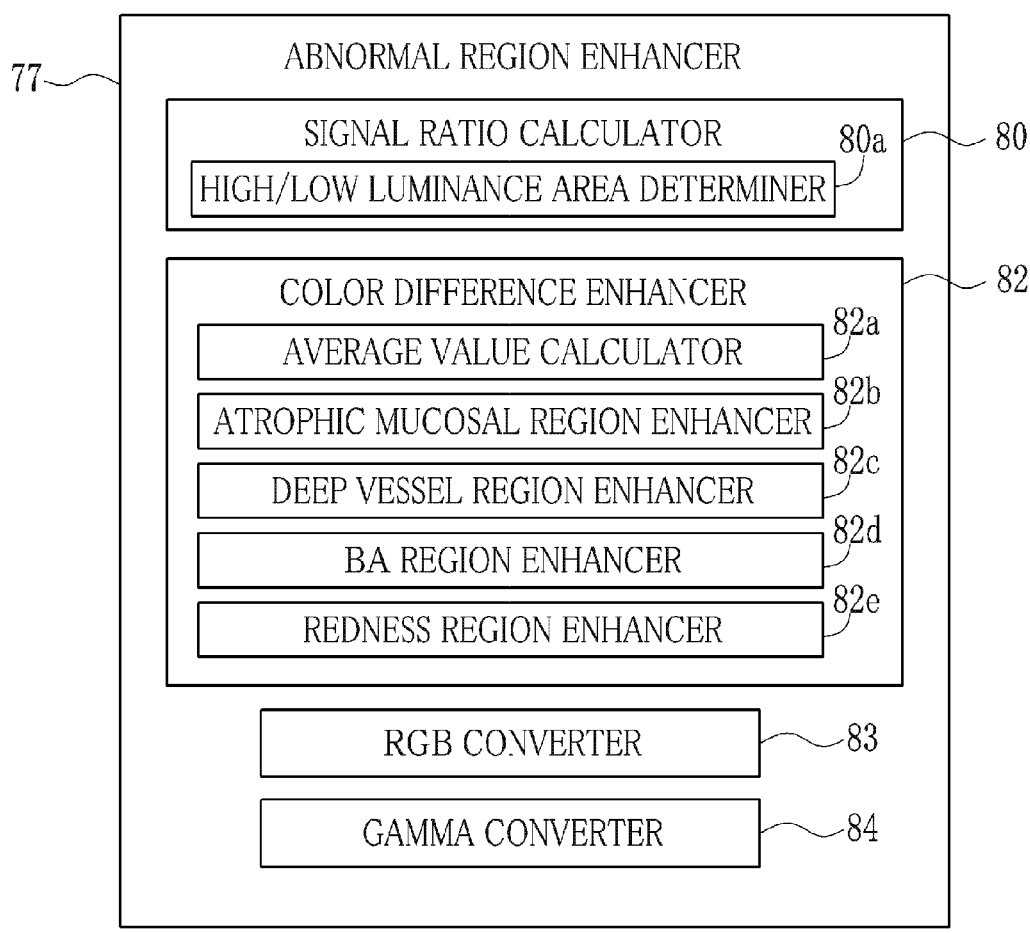
FIG. 5 is a block diagram illustrating internal configuration of an abnormal region enhancer.

As illustrated in FIG. 5, the abnormal region enhancer 77 comprises a signal ratio calculator 80, a color difference enhancer 82, an RGB converter 83, and a gamma converter 84. The signal ratio calculator 80 calculates a first signal ratio ($-\log(B/G)$) between the B signal and the G signal of the reflectance-linear RGB signals and a second signal ratio ($-\log(G/R)$) between the G signal and the R signal of the reflectance-linear RGB signals. The first and second signal ratios are normalized by the G and R signals, respectively, so that a distance from the object of interest and brightness of an observation area have little influence on the first and second signal ratios. However, the first and second signal ratios fluctuate significantly with a change in the density of the light absorbing components or a change in the internal mucosal structure because the first and second signal ratios contain the B and G signals, respectively, which correlate with a change in the density of the light absorbing components (hemoglobin) in mucosa, a change in the internal mucosal structure, or the like. Note that the above-described B signal corresponds to the B image signal outputted from the B pixel of the image sensor 48. The above-described G signal corresponds to the G image signal outputted from the G pixel of the image sensor 48. The above-described R signal corresponds to the R image signal outputted from the R pixel of the image sensor 48.

For example, the first signal ratio correlates with the depth of blood vessels (the position of the blood vessels in the depth direction of the mucosa), so that the first signal ratio of a portion with large blood vessels such as deep-layer blood vessels increases as the depth of the blood vessels increases and decreases as the depth of the blood vessels decreases. Both of the first signal ratio and the second signal ratio correlate with the absorption of hemoglobin, so that the first and second signal ratios increase as the absorption of light increases.

The signal ratio calculator 80 comprises a high/low luminance area determiner 80a for determining the high luminance area and the low luminance area in the reflectance-linear RGB signals. In the high luminance area, the luminance value is greater than or equal to an upper limit value. In the low luminance area, the luminance value is less than or equal to a lower limit value. The high and low luminance areas include significant noise. In a case where the first or second signal ratio is calculated using signals in the high or low luminance area, the first or second signal ratio may take an extremely large value, enhancing the noise. For this reason, a level of the enhancement process for an area determined as the high or low luminance area by the high/low luminance area determiner 80a is suppressed (suppression process), as compared with the level of the enhancement process for another area, which will be described below. Note that the R signal of the reflectance-linear RGB signals varies in association with the amount of reflection light. Therefore it is preferred to determine the high and low luminance areas based on the R signal.

Figure 6:
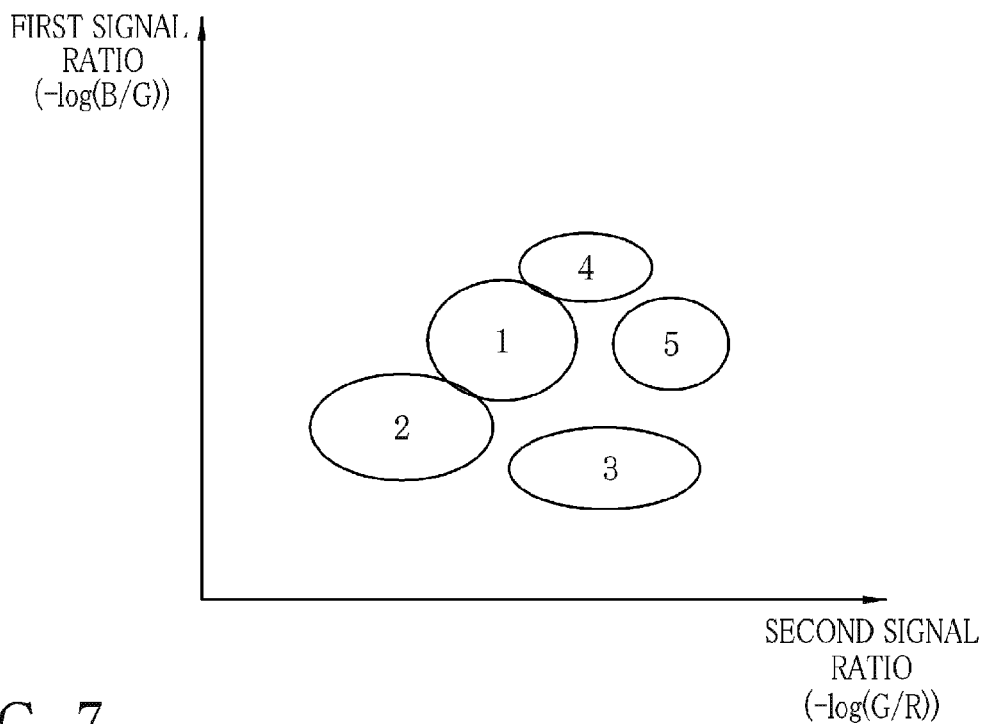
FIG. 6 is a graph illustrating a positional relationship among first to fifth areas.

The color difference enhancer 82 comprises an average value calculator 82a, an atrophic mucosal region enhancer 82b, a deep blood vessel region enhancer 82c, a BA region enhancer 82d, and a redness region enhancer 82e. The color difference enhancer 82 increases a difference between the first and second signal ratios in the first area and the first and second signal ratios in each of the second to fifth areas in the two-dimensional space (the vertical axis: the first signal ratio ($-\log(B/G)$, the horizontal axis: the second signal ratio ($-\log(G/R)$) shown in FIG. 6, to increase a color difference between the normal mucosa and an abnormal region (the atrophic mucosa, BA (Brownish area), redness, or the like) in the observation area.

Figure 7:
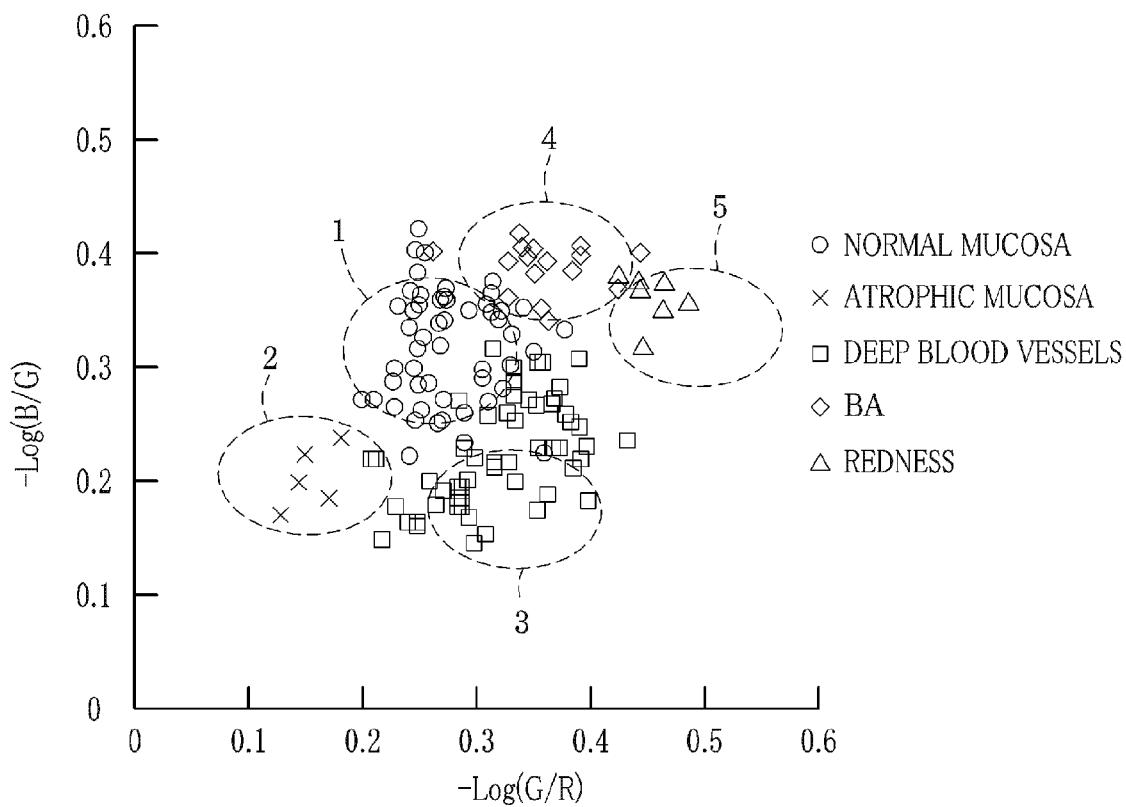
FIG. 7 is a graph illustrating actual measurement data representing distribution of first and second signal ratios obtained using the special light, in which the emission intensity of blue laser beams is greater than the emission intensity of blue violet laser beams, for illumination.

The actual measurement data shown in FIG. 7 indicates that the first area mostly contains the first and second signal ratios corresponding to the normal mucosa. In FIG. 7, "o" denotes the normal mucosa. The first area is located substantially at the center in the two-dimensional space. The second area mostly contains the first and second signal ratios corresponding to the atrophic mucosa. In FIG. 7, "x" denotes the atrophic mucosa. The second area is located at the lower left of the first area in the two-dimensional space. The third area mostly contains the first and second signal ratios corresponding to deep blood vessels. In FIG. 7, "□" denotes the deep blood vessels. The third area is located at the lower right of the first area. The fourth area mostly contains the first and second signal ratios corresponding to BA. In FIG. 7, "◇" denotes the BA. The fourth area is located at the upper right of the first area. The fifth area mostly contains the first and second signal ratios corresponding to redness. In FIG. 7, "△" denotes the redness. The fifth area is located to the right of the first area. Note that the "specific area" according to an aspect of the present invention includes at least one of the second area, the third area, the fourth area, and the fifth area.

The average value calculator 82a calculates the average value of the first and second signal ratios in the first area. The average value calculator 82a performs polar coordinate conversion of the calculated average value to obtain a first area average value (rm, θm) that has been subjected to the polar coordinate conversion.

Figure 8:
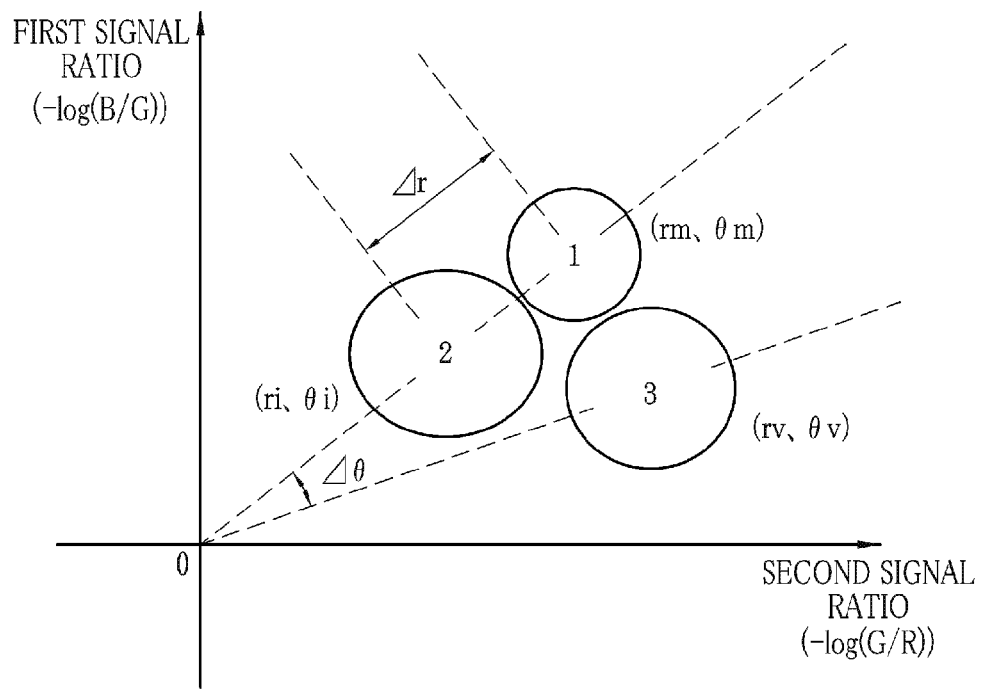
FIG. 8 is an explanatory view illustrating positions of a second area and a third area in a two-dimensional space (the vertical axis: −log (B/G), the horizontal axis: −log(G/R)) before a color difference enhancement process.
Figure 9:
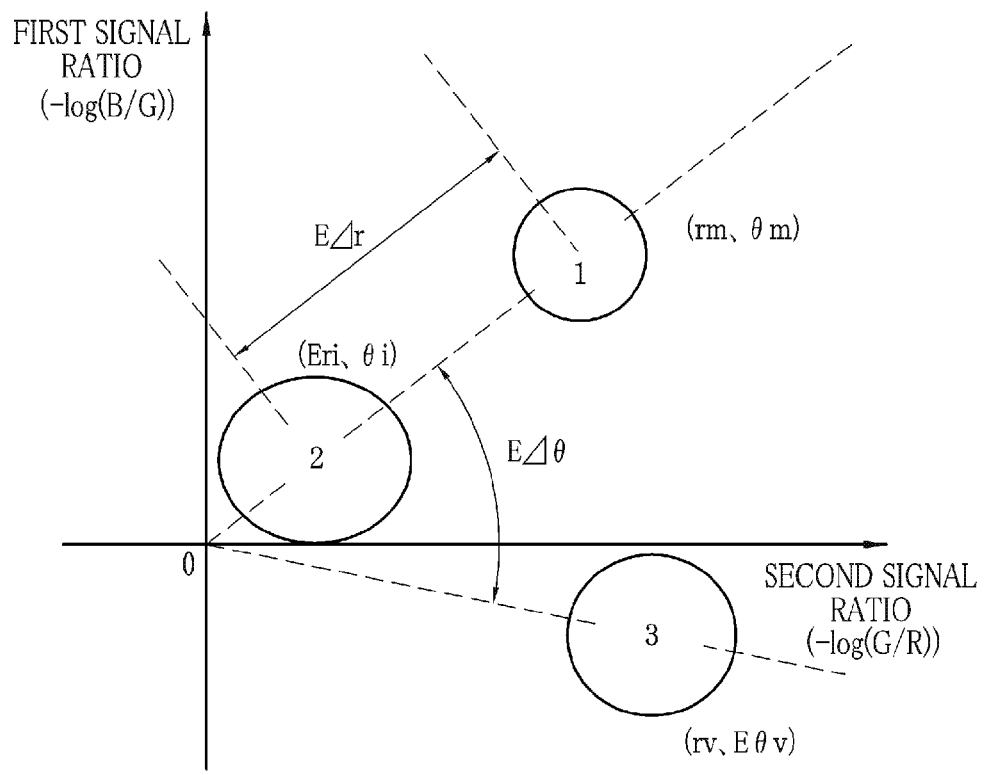
FIG. 9 is an explanatory view illustrating positions of the second area and the third area in the two-dimensional space after the color difference enhancement process.

The atrophic mucosal region enhancer 82b performs polar coordinate conversion of the first and second signal ratios in the second area to obtain a second area signal (ri, θi) that has been subjected to the polar coordinate conversion. The atrophic mucosal region enhancer 82b performs a first expansion process for expanding (increasing) a radial coordinate difference Δr between the first area average value (rm, θm) and the second area signal (ri, θi), which have been subjected to the polar coordinate conversion, as illustrated in FIG. 8. The first expansion process is performed using an expression (1) shown below. Thereby an enhanced second area signal (Eri, θi) is obtained. As illustrated in FIG. 9, a radial coordinate difference EΔr between the enhanced second area signal (Eri, θi) and the first area average value (rm, θm) is greater than Δr.

$$Eri = (ri - rm) \cdot \alpha + rm \quad (\alpha \geq 1) \tag{1}$$

Figure 10:
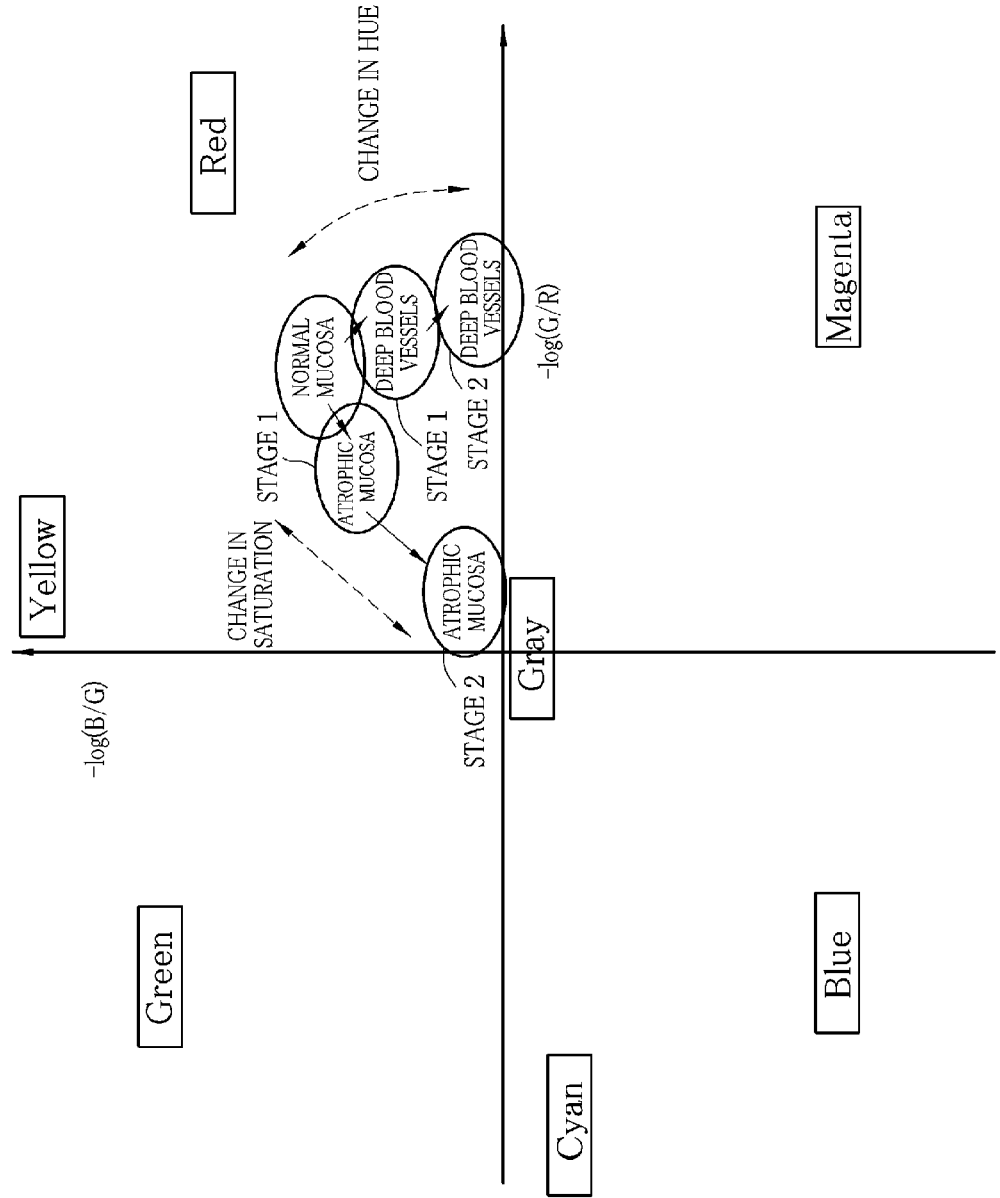
FIG. 10 is an explanatory view illustrating changes in distribution of the first and second signal ratios with the progress of atrophic gastritis and a relationship between the two-dimensional space and chromaticity.

As illustrated in FIGS. 8 and 9, the atrophic mucosal region enhancer 82b performs the first expansion process to expand the radial coordinate difference Δr in a direction to reduce the saturation while maintaining the hue unchanged. The color is changed through the first expansion process in accordance with the change in the color of mucosa fading with the progress of the atrophic gastritis as illustrated in FIG. 10. In FIG. 10, stage 2 means that the atrophic gastritis is more advanced than that at stage 1. The difference between the atrophic mucosal region and the normal mucosal region is small at the stage 1. At the stage 2, on the other hand, the difference between the atrophic mucosal region and the normal mucosal region is increased by reducing only the saturation while the hue is maintained unchanged.

In the special light image displayed on the monitor 18 based on the enhanced second area signal (Eri, θi), the atrophic mucosal region clearly appears in colors different from those of the normal mucosal region and the color of the atrophic mucosal region is substantially the same as the actual color of the mucosa with the atrophic gastritis. Thereby the border between the normal mucosal region and the atrophic mucosal region is determined reliably. The first expansion process is especially effective for the cases where a color difference between the normal mucosal region and the atrophic mucosal region is small (for example, for the cases where the atrophic gastritis is progressing, corresponding to the group B or the group C of the ABC screening).

Note that the expansion in the hue direction (the expansion of an angular coordinate difference) may be performed in addition to the expansion in the saturation direction (the expansion of a radial coordinate difference) to further enhance the difference in color between the normal mucosal region and the atrophic mucosal region. The expansion is suppressed by reducing the value α in the high and low luminance areas (suppression process). In a case where the atrophy is in a highly advanced stage, the color of the atrophic mucosal region becomes bluish when the value α in the expression (1) is too large. In this case, the value α is reduced (the value α is adjusted by operating the console 20) to make the color of the atrophic mucosal region the same as the actual color (the faded color) of the atrophic mucosa.

The deep blood vessel region enhancer 82c performs the polar coordinate conversion of the first and second signal ratios in the third area to obtain a third area signal (rv, θv) that has been subjected to the polar coordinate conversion, and performs a second expansion process for expanding (increasing) an angular coordinate difference Δθ between the first area average value (rm, θm) and the third area signal (rv, θv), which have been subjected to the polar coordinate conversion (see FIG. 8). The second expansion process is performed using an expression (2) shown below. Thereby an enhanced third area signal (rv, Eθv) is obtained. As illustrated in FIG. 9, an angular coordinate difference EΔθ between the enhanced third area signal (rv, Eθv) and the first area average value (rm, θm) is greater than Δθ.

$$E\theta v = (\theta v - \theta m) \cdot \beta + \theta m \quad (\beta \geq 1) \tag{2}$$

As illustrated in FIGS. 8 and 9, the second expansion process performed by the deep blood vessel region enhancer 82c is to expand the angular coordinate difference Δθ in the hue direction while the saturation is maintained unchanged. The color is changed through the second expansion process in accordance with the change in the color of the deep blood vessels becoming more apparent as the atrophic gastritis progresses as illustrated in FIG. 10. In FIG. 10, the stage 2 means that the atrophic gastritis is at a more advanced stage than the stage 1. The difference between the atrophic mucosal region and the normal mucosal region is small at the stage 1. At the stage 2, on the other hand, the difference between the atrophic mucosal region and the normal mucosal region is increased by changing only the hue while the saturation is maintained substantially unchanged.

Thereby, the special light image that is displayed on the monitor 18 based on the enhanced third area signal (rv, Eθv) clearly shows the deep blood vessel region in colors that differ from those of the normal mucosal region. Because the colors of the deep blood vessels are apparent in the special light image, the deep blood vessels are seen positively through the atrophic mucosa. Thus, the border between the normal mucosal region and the deep blood vessel region is determined reliably. The second expansion process is especially effective for the cases where the deep blood vessels are not clearly seen through the atrophic mucosa (for example, for the cases where the atrophy is progressing, corresponding to the group B or the group C of the ABC screening).

Note that the expansion in the saturation direction (the expansion of the radial coordinate difference) may be performed in addition to the expansion in the hue direction (the expansion of the angular coordinate difference) to further enhance the difference in color between the normal mucosal region and the deep blood vessel region. With regard to the high and low luminance areas, the value β is reduced to suppress the expansion (suppression process). In a case where the atrophy is highly progressed, the color of the deep blood vessel region is magenta-tinted if the value β of the expression (2) is too large. In this case, the value β is reduced (the value α is adjusted by operating the console 20) to make the color of the deep blood vessel region the same as the actual color of the deep blood vessels.

The BA region enhancer 82d performs the polar coordinate conversion of the first and second signal ratios in the fourth area, to obtain a fourth area signal (rk, θk) that has been subjected to the polar coordinate conversion. The BA region enhancer 82d performs a third expansion process with the use of expressions (3) and (4) shown below. The third expansion process expands (increases) the radial coordinate difference Δr and the angular coordinate difference Δθ between the first area average value (rm, θm) and the fourth area signal (rk, θk) that have been subjected to the polar coordinate conversion. Thereby, an enhanced fourth area signal (Erk, Eθk) in which both of the radial coordinate difference Δr and the angular coordinate difference Δθ are expanded is obtained.

$$Erk = (rk - rm) \cdot \alpha + rm \quad (\alpha \geq 1) \tag{3}$$

$$E\theta k = (\theta k - \theta m) \cdot \beta + \theta m \quad (\beta \geq 1) \tag{4}$$

A special light image displayed on the monitor 18 based on the enhanced fourth area signal (Erk, Eθk) clearly shows the BA region in colors that differ from those of the normal mucosal region. Thereby the border between the normal mucosal region and the BA region is determined reliably. Note that the BA region enhancer 82d may expand one of the radial coordinate difference Δr and the angular coordinate difference Δθ, instead of increasing both of the radial coordinate difference Δr and the angular coordinate difference Δθ. The values α and β for the high and low luminance areas are reduced to suppress the expansion (suppression process).

The redness region enhancer 82e performs the polar coordinate conversion of the first and second signal ratios in the fifth area, to obtain a fifth area signal (rj, θj) that has been subjected to the polar coordinate conversion. The redness region enhancer 82e performs a fourth expansion process with the use of expressions (5) and (6) shown below. The fourth expansion process expands (increases) the radial coordinate difference Δr and the angular coordinate difference Δθ between the first area average value (rm, θm) and the fifth area signal (rj, θj) that have been subjected to the polar coordinate conversion. Thereby an enhanced fifth area signal (Erj, Eθj) in which both of the radial coordinate difference Δr and the angular coordinate difference Δθ are expanded is obtained.

$$Erj=(rj-rm)\cdot\alpha+rm(\alpha\geq 1) \quad (5)$$

$$E\theta j=(\theta j-\theta m)\cdot\beta+\theta m(\beta\geq 1) \quad (6)$$

A special light image displayed on the monitor 18 based on the enhanced fifth area signal (Erj, Eθj) clearly shows the redness region in colors that differ from those of the normal mucosal region. Thereby, the border between the normal mucosal region and the redness region is determined reliably. Note that the redness region enhancer 82e may increase one of the radial coordinate difference Δr and the angular coordinate difference Δθ, instead of increasing both of the radial coordinate difference Δr and the angular coordinate difference Δθ. The values α and β for the high and low luminance areas are reduced to suppress the expansion (suppression process).

The RGB converter 83 converts the enhanced color difference signal (the enhanced atrophic mucosa signal, the enhanced deep blood vessel signal, the enhanced BA signal, and the enhanced redness signal), which are generated by the color difference enhancer 82, back into the RGB image data. The RGB converter 83 converts the enhanced color difference signal, which represents a value in a polar coordinate space, back into the RGB values. The gamma converter 84 performs the gamma conversion on the RGB image data whose color difference has been enhanced. Thereby the color-difference-enhanced RGB image data having the tone suitable for an output device such as the monitor 18 is generated.

Figure 11:
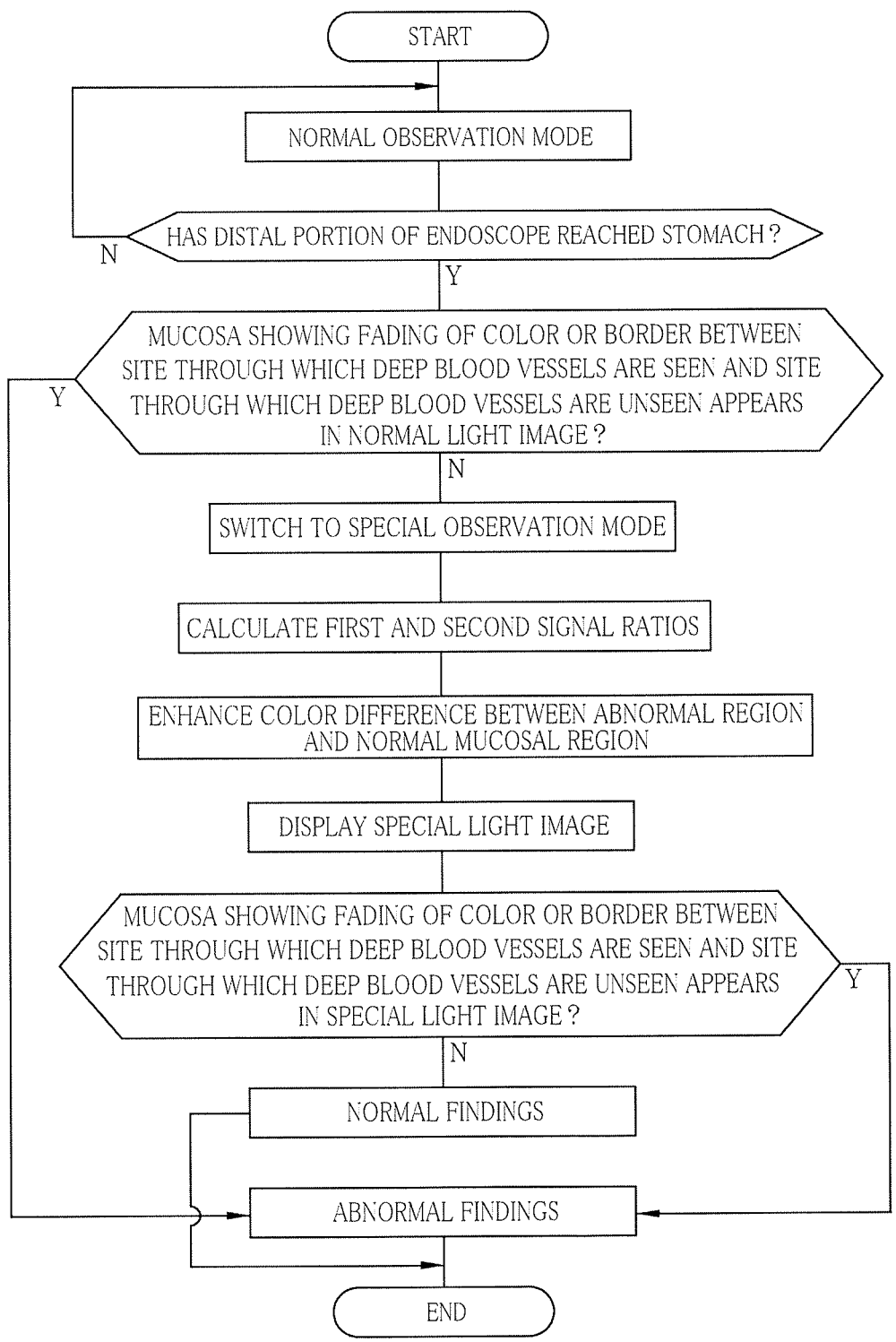
FIG. 11 is a flowchart illustrating steps in diagnosing the atrophic gastritis.

Hereinafter, referring to a flowchart in FIG. 11, steps of this embodiment are described. First, the mode is set to the normal observation mode, and the insertion section 21 of the endoscope 12 is inserted into a body cavity. After the distal portion 24 of the insertion section 21 reaches the stomach, the presence or absence of the atrophic gastritis is diagnosed. In a case where the color of the mucosa is faded or a border (referred to as the endoscopic glandular border) between a site through which dendritic deep blood vessels are seen and a site through which the dendritic deep blood vessels cannot be seen appears in the normal light image, a doctor determines it as pathologic findings (abnormal condition), being the emergence of a lesion e.g. the stomach cancer caused by the atrophic gastritis (a method for diagnosing based on Kimura-Takemoto classification). Note that it has also been known that atrophy of gastric mucosa caused by infection of Helicobacter pylori leads to emergence of the stomach cancer.

In a case where the mucosa showing fading of color or the presence of the endoscopic glandular border cannot be found in the normal light image, the mode SW 22b is operated to switch the mode to the special observation mode to diagnose more reliably. Upon switching the mode to the special observation mode, the special light that includes both of the blue laser beams and the blue violet laser beams is emitted. The first and second signal ratios are calculated based on the RGB image signals generated during the emission of the special light.

Based on the calculated first and second signal ratios, the average value (the first area average value) of the first and second signal ratios in the first area is calculated and this first area average value is subjected to the polar coordinate conversion. The first and second signal ratios in each of the second to fifth areas are subjected to the polar coordinate conversion. Thereby, the second to fifth area signals that have been subjected to the polar coordinate conversion are generated. The radial coordinate difference or the angular coordinate difference between the first area average value, which has been subjected to the polar coordinate conversion, and each of the second to fifth area signals, which have been subjected to the polar coordinate conversion, is expanded. Thereby the enhanced color difference signals (the enhanced second area signal, the enhanced third area signal, the enhanced fourth area signal, and the enhanced fifth area signal), in which the color difference between the normal mucosa and the abnormal region is enhanced, are generated. The monitor 18 displays the special light image based on the enhanced color difference signal(s).

In a case where there is no atrophy of the stomach, the mucosa is displayed in its normal color in the special light image. In this case, a doctor determines it as normal findings with no lesion such as the stomach cancer caused by the atrophic gastritis. In a case where there is a slight progress of the atrophy of the stomach, the atrophic mucosa is displayed in faded colors and the deep blood vessels that are to be seen through the atrophic mucosa are displayed. Thereby the endoscopic glandular border is displayed clearly. A doctor is able to determine it as the pathologic findings where a lesion such as the stomach cancer caused by the atrophic gastritis is present even if the atrophic mucosa shows little fading of color and not so many of the deep blood vessels are seen through the mucosa in the actual stomach.

In the above embodiment, note that the special light including the blue narrowband component (the blue laser beams and the blue violet laser beams), to which the light absorbing material of the mucosa has high light absorption properties, is used in the special observation mode, so that the color differences among the atrophic mucosa, the deep blood vessel region, and the BA region, which are in the abnormal region, and the normal mucosal region in the observation area are greater than in the case where the illumination light including the blue broadband component is used. The reason for this will be described below.

Figure 12:
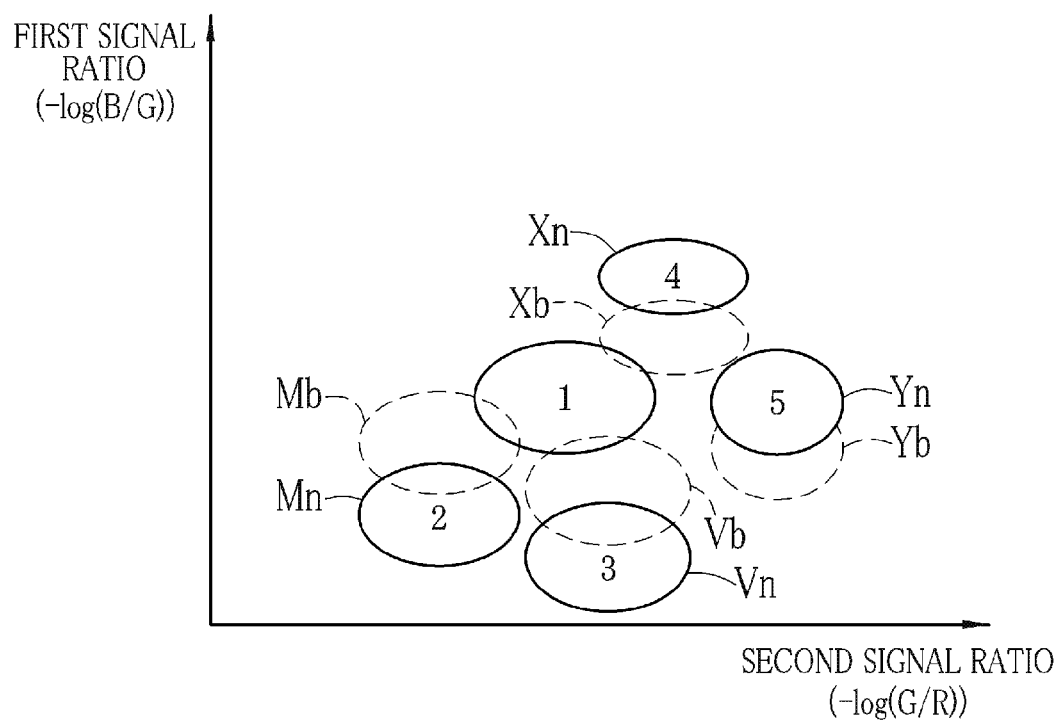
FIG. 12 is an explanatory view illustrating a positional relationship between a first area and each of second to fifth areas, for the case where the special light including the blue narrowband light is used, and a positional relationship between the first area and each of second to fifth areas, for the case where the illumination light including the blue broadband light is used, in a two-dimensional space.

FIG. 12 illustrates the positions of the second to fifth areas in the two-dimensional space in a case where the special light including a blue narrowband component (the blue laser beams and the blue violet laser beams) is used in a manner similar to the above embodiment, and the positions of the first to fifth areas in the two-dimensional space in a case where the illumination light including a blue broadband component (for example, 400 to 520 nm) is used. In FIG. 12, the second area Mn is obtained in a case where the special light including the blue narrowband component is used. The second area Mn represents an area that mostly contains signals corresponding to the atrophic mucosa. The second area Mb is obtained in a case where the illumination light including the blue narrowband component is used. The second area Mb represents an area that mostly contains signals corresponding to the atrophic mucosa.

A third area Vn, a fourth area Xn, and a fifth area Yn are obtained in a case where the special light including the blue narrowband component is used. The third area Vn, the fourth area Xn, and the fifth area Yn represent an area that mostly contains signals corresponding to the deep blood vessel region, an area that mostly contains signals corresponding to the BA region, and an area that mostly contains signals corresponding to the redness region, respectively. A third area Vb, a fourth area Xb, and a fifth area Yb are obtained in a case where the special light including the blue broadband component is used. The third area Vb, the fourth area Xb, and the fifth area Yb represent an area that mostly contains signals corresponding to the deep blood vessel region, an area that mostly contains signals corresponding to the BA region, and an area that mostly contains signals corresponding to the redness region, respectively. As illustrated in FIG. 12, the difference between the first area and each of the second area Mn, the third area Vn, and the fourth area Xn is large, whereas there is a little difference between the first area and each of the second area Mb, the third area Vb, and the fourth area Xb. Thus, the difference between the first area and each of the second to fourth areas Mn, Vn, and Xn is increased sufficiently by using the special light including the blue narrowband component. In addition, the color difference enhancer 82 expands (increases) the radial coordinate difference or the angular coordinate difference to further increase the difference between the first area and each of the second to fourth areas Mn, Vn, and Xn. Thus, the color difference between the normal mucosa and each of the atrophic mucosal region, the deep blood vessel region, and the BA region in the case where the special light including the blue narrowband component is used is greater than in the case where the illumination light including the blue broadband component is used, by the difference between the first area and each of the second to fourth areas Mn, Vn, and Xn caused by the blue narrowband component.

With respect to the fifth area Yn, as compared with the fifth area Yb, the difference between the fifth area Yn and the first area hardly differs from the difference between the fifth area Yb and the first area. Accordingly, the color difference between the normal mucosa and the redness region does not vary much, regardless of using the special light including the blue narrowband component or the illumination light including the blue broadband component.

As described above, the magnitude of the color difference between the normal region and the abnormal region varies depending on whether the special light includes the blue narrowband component. This is mainly due to factors that are dependent on the distribution density of the light absorbing material such as the blood density in the mucosa. This is explained using the relationship (see FIG. 13) between the reflection density, and the absorption coefficient (see FIG. 14 for the distribution of the absorption coefficient of hemoglobin) and the distribution density of the light absorbing material (mainly hemoglobin in digestive organ) in the mucosa. Note that, in a case where the reflection density is defined as "(−log (Bch) (the reflectance of the light incident on the B ch of the image sensor)))", the first signal ratio varies with a change in the reflection density.

Figure 13:
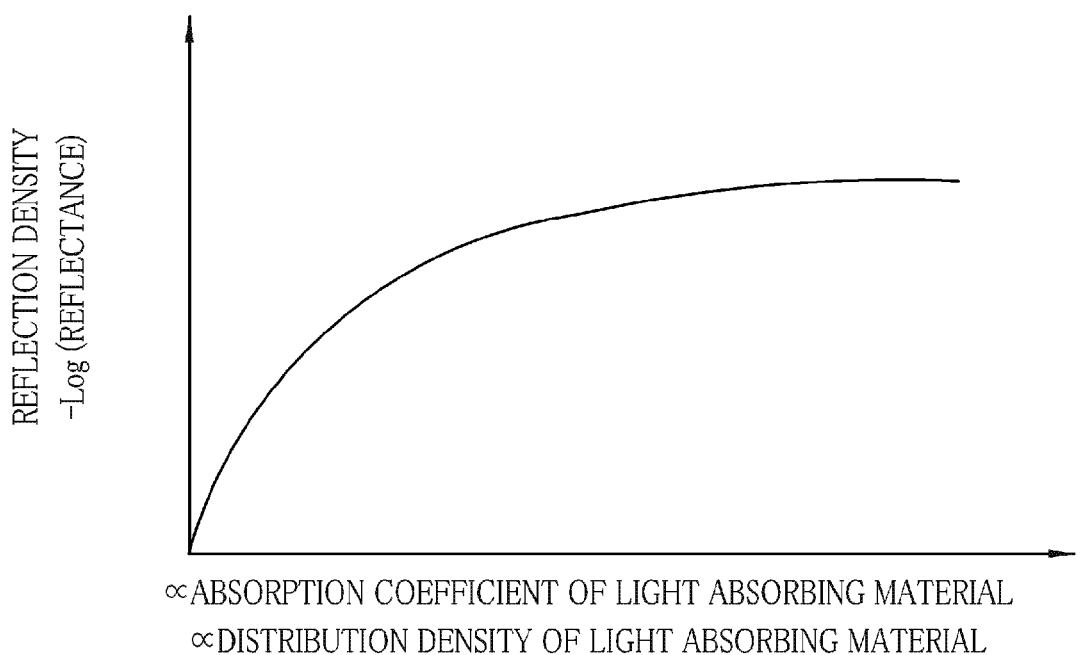
FIG. 13 is a graph illustrating a relationship between reflection density, and absorption coefficient and distribution density of a light absorbing material.
Figure 14:
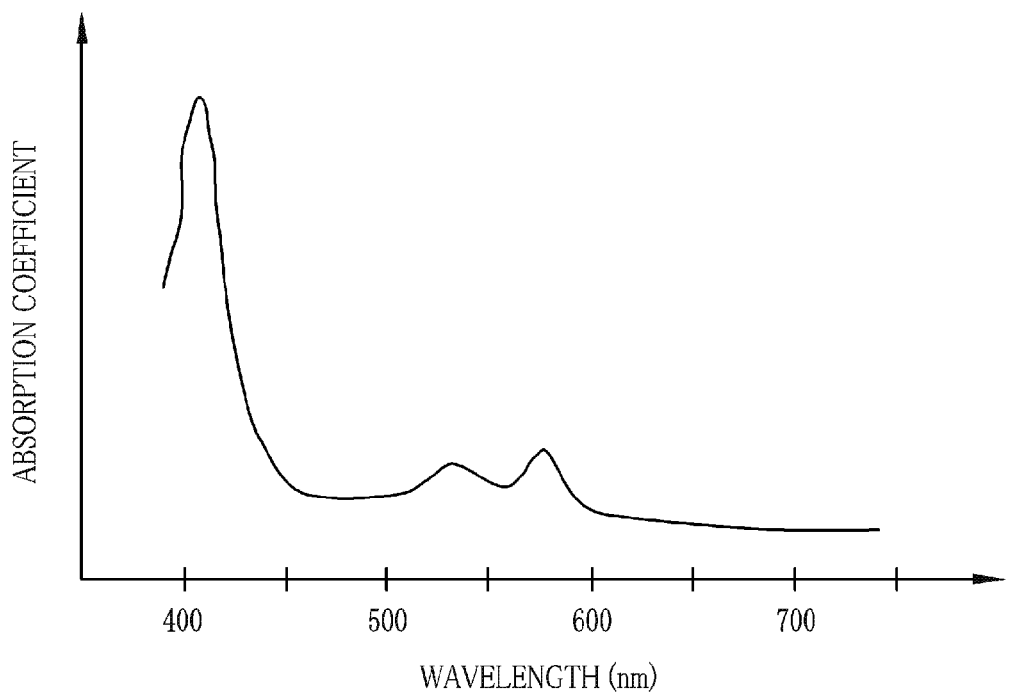
FIG. 14 is a graph illustrating distribution of absorption coefficient of hemoglobin.

According to FIG. 13, the reflection density increases nonlinearly relative to the absorption coefficient and the distribution density of the light absorbing material. The magnitude of the reflection density increases as the light absorption and the distribution density in the mucosa increase. With regard to the increase in the amount of reflection density, the reflection density increases significantly even with a small increase in the absorption or the density in a case where the light absorption is low and the distribution density is low, whereas the reflection density does not increase much with the increase in the absorption or the density in a case where the light absorption is high and the distribution density is high.

Referring to the relationship of the distribution of the reflection density illustrated in FIG. 13, the color difference between the normal mucosa and the abnormal region is described for each of the cases where reflection light (hereinafter denoted as "narrowband light 445 nm+405 nm") of the mixed narrowband light of the blue laser beams (445 nm) and the blue violet laser beams (405 nm), reflection light (hereinafter denoted as "narrowband light 405 nm") of the blue violet laser beams (405 nm), reflection light (hereinafter denoted as "narrowband light 445 nm") of the blue laser beams (445 nm), or reflection light (hereinafter denoted as "broadband B light") of the blue light in a broadband wavelength range (for example, 400 to 500 nm) in a blue region is incident on the B ch of the image sensor 48.

Figure 15:
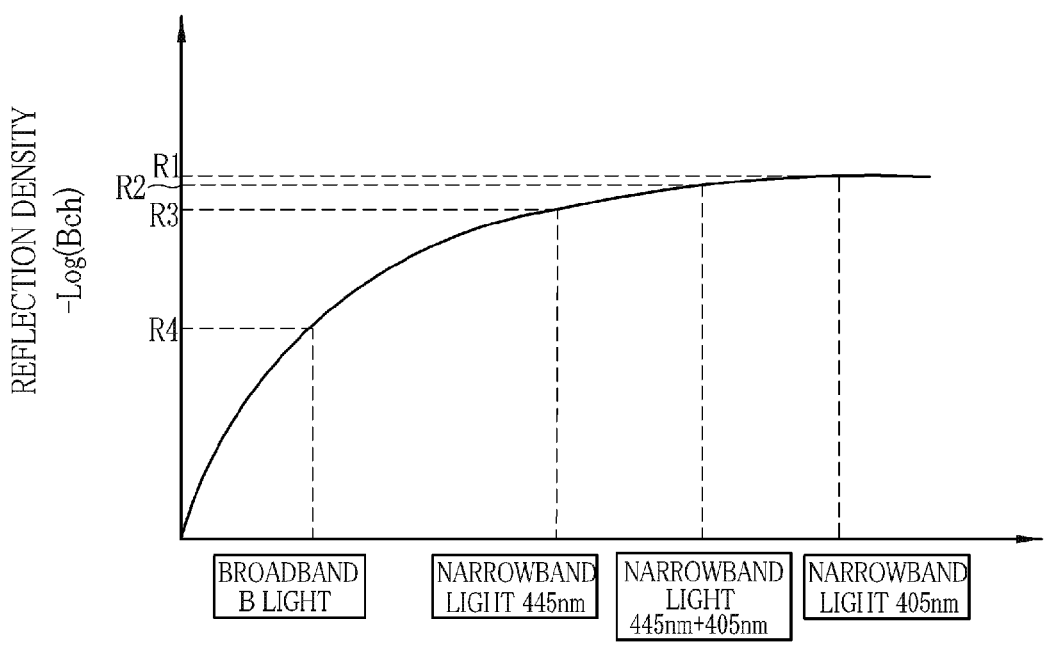
FIG. 15 is a graph illustrating distribution of reflection density of a BA (brownish area) region.

Referring to the reflection density distribution in the BA region illustrated in FIG. 15, the reflection density R1 of the narrowband light 405 nm is the highest. The reflection density R1 is followed by the reflection density R2 of the narrowband light 445 nm+405 nm. The reflection density R3 of the narrowband light 445 nm is lower than the reflection densities R1 and R2. The reflection density R4 of the broadband B light is the lowest. This magnitude relationship is due to the relationship among the magnitude of the light absorption "the narrowband light 405 nm>the narrowband light 445 nm+405 nm>the narrowband light 445 nm>the broadband B light" (see FIG. 14).

Figure 16:
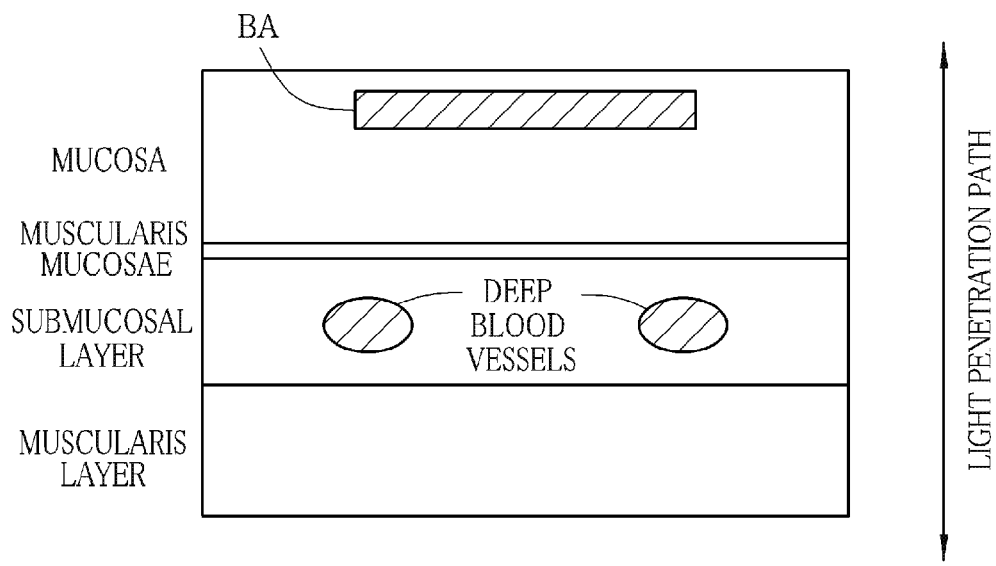
FIG. 16 is an explanatory view illustrating the BA region, in which blood density in mucosal layer is locally high in a surface layer.

The difference between the reflection density R4 of the broadband B light and each of the reflection densities R1 to R3 of the narrowband B light (the narrowband light 405 nm, the narrowband light 445 nm+405 nm, and the narrowband light 445 nm) is relatively large. This is because the reflection density R4 of the broadband B light is especially low. The difference in reflection density between the normal mucosa and the BA region in the case where the narrowband B light is used is greater than in the case where the broadband B light is used. The reflection density R4 of the broadband B light is low because the BA region is distributed narrowly only in a relatively shallow location in the mucosa (see FIG. 16), so that the blood density along a light penetration path is relatively low. In addition, the broadband B light includes the wavelengths around 500 nm, at which the absorption by the hemoglobin is low. The difference in reflection density (for example, the difference between the reflection density R1 and the reflection density R2) caused by the difference in wavelength of the narrowband B light is relatively larger than in the case of the redness region. This is because the blood density along the light penetration path in the BA region is low, so that the difference in light absorption caused by the difference in wavelength significantly influences the difference in reflection density.

Figure 17:
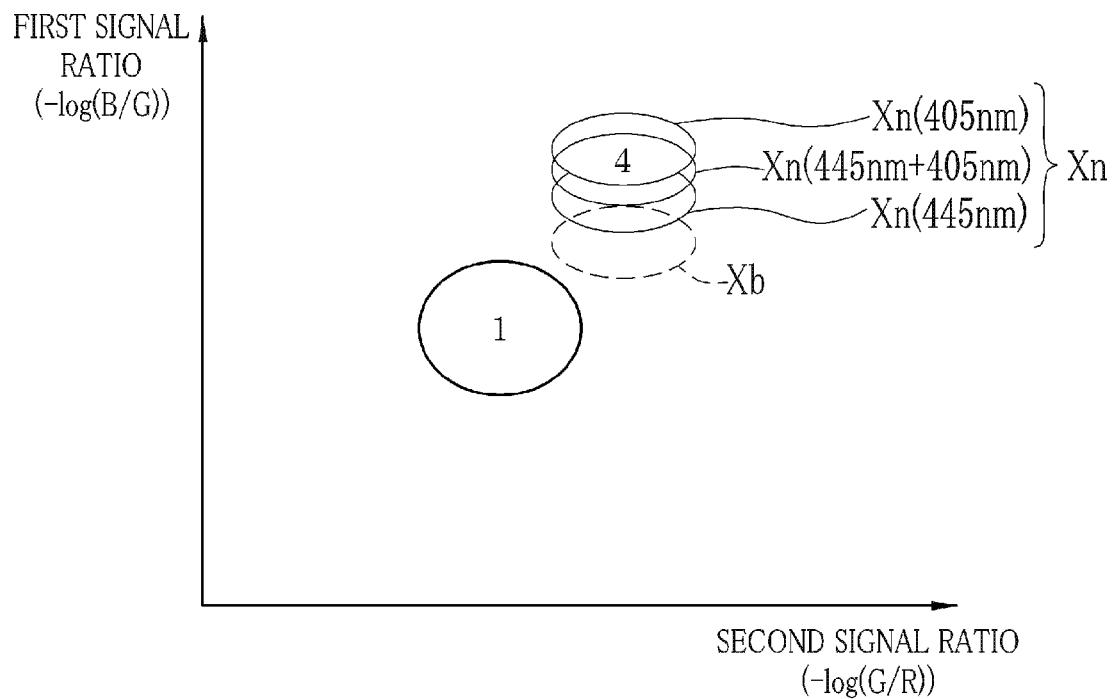
FIG. 17 is an explanatory view illustrating a positional relationship in a two-dimensional space between the fourth area, for the case where narrowband B light is used, and the fourth area for the case where broadband B light is used.

As illustrated in FIG. 17, the difference in the first signal ratio between the first area and the fourth area Xn in the case where the narrowband B light is used is greater than that between the first area and the fourth area Xb in the case where the broadband B light is used, because the BA region has the above-described reflection density. In the case where the positional relationship between the first area and each of the fourth area Xn (405 nm) corresponding to the narrowband light 405 nm, the fourth area Xn (445 nm+405 nm) corresponding to the narrowband light 445 nm+405 nm, and the fourth area Xn (445 nm) corresponding to the narrowband light 445 nm, which are obtained by using the narrowband B light, is compared with each other, the difference between the first area and the fourth area increases as the wavelength of the light becomes shorter. Thus, the difference between the first area and the fourth area is increased by using the narrowband B light. Accordingly, the color difference between the normal mucosal region and the BA region is further increased.

Note that each of the blood densities along their light penetration paths in the atrophic mucosal region and the deep blood vessel region is lower than that in the redness region, as in the case of the BA region. The atrophic mucosal region and the deep blood vessel region are similar to the BA region in reflection density distribution, so that the difference between the first area and each of the second and third areas is increased by using the light of shorter wavelengths, as in the case of the BA region. Thus, the difference between the first area and each of the second and third areas is increased by using the narrowband B light. Accordingly, the color difference between the normal mucosal region and each of the atrophic mucosal region and the deep blood vessel region is further increased.

Figure 18:
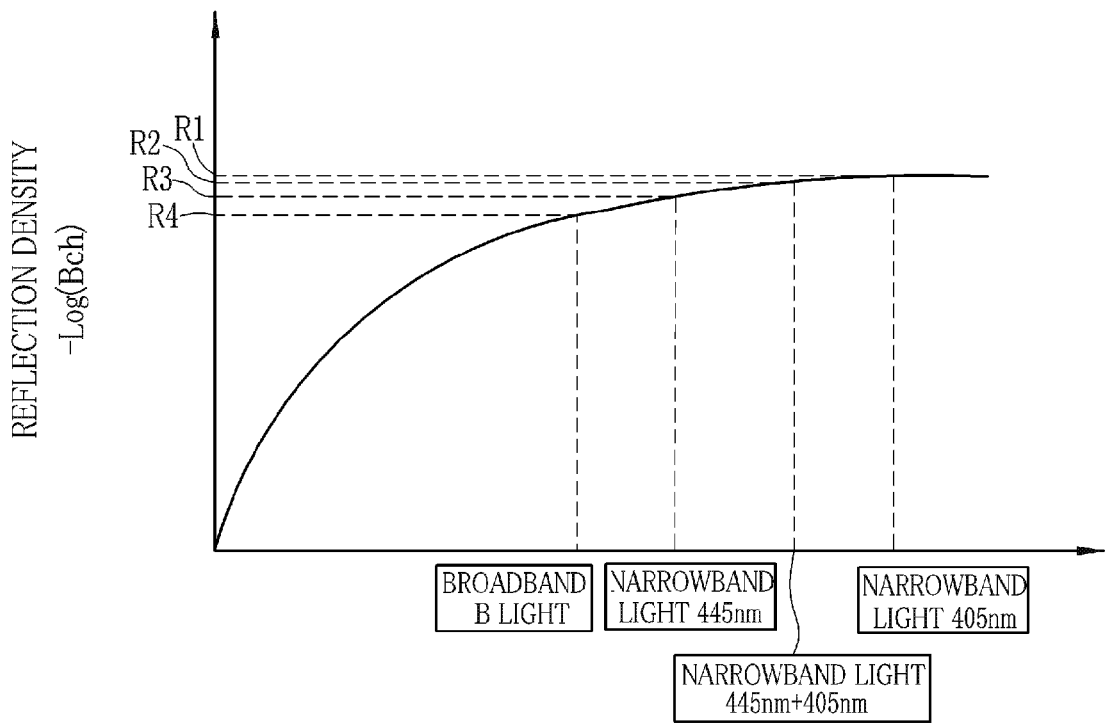
FIG. 18 is a graph illustrating distribution of reflection density of a redness region.
Figure 19:
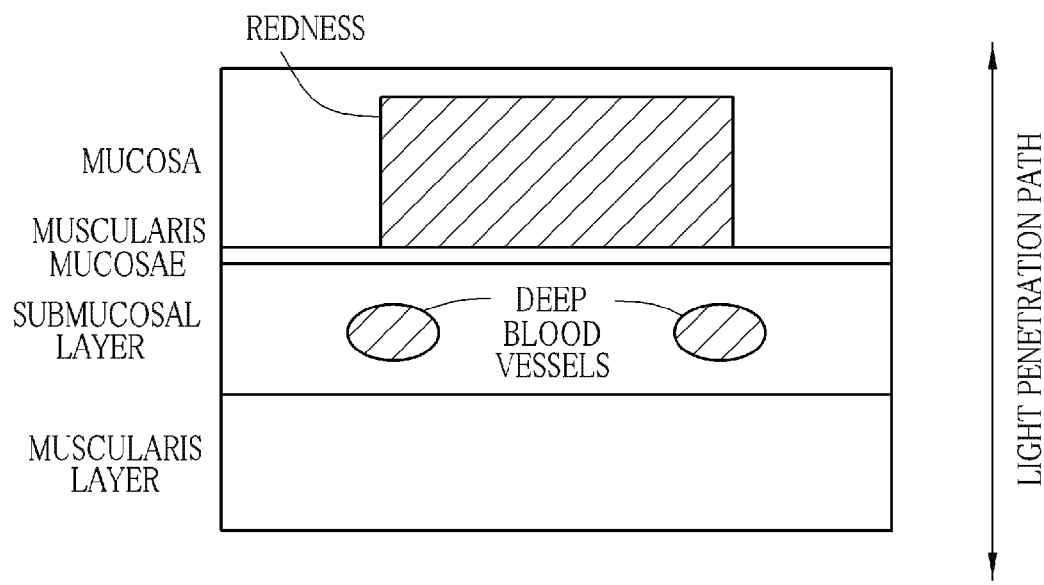
FIG. 19 is an explanatory view illustrating the redness region, in which the blood density in the mucosal layer is locally high across the mucosa.

As illustrated in FIG. 18, the magnitude relationship among the reflection densities R1 to R4 in the redness region is similar to that in the BA region or the like. However, the difference between the reflection density R4 of the broadband B light and each of the reflection densities R1 to R3 of the narrowband B light is relatively smaller than in the case of the BA region or the like. This is because the reflection density R4 of the broadband B light is higher than that in the BA region or the like. The reflection density R4 of the broadband B light is relatively high because the redness is widely distributed from shallow to deep locations in the mucosa as illustrated in FIG. 19, so that the blood density along the light penetration path is relatively high. With regard to the narrowband B light, the difference in reflection density (for example, the difference between the reflection density R1 and the reflection density R2) caused by a difference in wavelength is not so large as compared with that in the BA region. This is because the blood density in the redness region along the light penetration path is relatively high as compared with that in the BA region or the like. The difference in wavelength may cause a difference in light absorption but it has a limited influence on the difference in reflection density.

Figure 20:
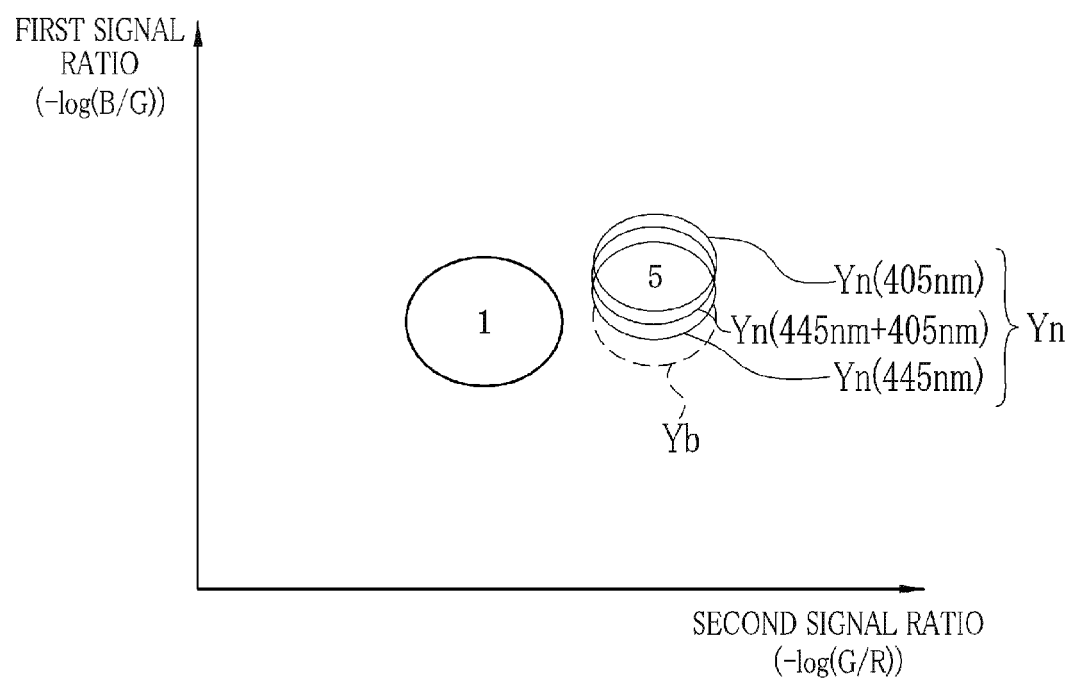
FIG. 20 is an explanatory view illustrating a positional relationship in a two-dimensional space between the fifth area, for the case where the narrowband B light is used, and the fifth area for the case where the broadband B light is used.

As illustrated in FIG. 20, because the redness region has the above-described reflection density, the difference between the first area and the fifth area Yn in the case where the narrowband B light is used does not differ much from the difference between the first area and the redness region Yb in the case where the broadband B light is used. With regard to the cases where the narrowband B light is used, the positional relationship between the first area and each of the fifth area Yn (405 nm) corresponding to the narrowband light 405 nm, the fifth area Yn (445 nm+405 nm) corresponding to the narrowband light 445 nm+405 nm, and the fifth area Yn (445 nm) corresponding to the narrowband light 445 nm is compared with each other. There is little difference between the first area and each of the fifth areas. Thus, the narrowband B light does not increase the difference between the first area and the fifth area much. Accordingly, the color difference between the normal mucosal region and the redness region is not increased much.

However, in a case where the redness region is of a mild level (mild redness region) and not a high blood density region such as advanced redness or bleeding, the difference in reflection density between the normal mucosal region and the mild redness region in the case where the narrowband B light is used is greater than in the case where the broadband B light is used. Accordingly, the color difference between the normal region and the mild redness region is increased by using the narrowband B light.

The above describes the change in the first signal ratio in the case where the wavelength range of the B light to be incident on the B ch of the image sensor 48 is narrowed (that is, the positions of the second to fifth areas shift in the vertical axis direction in the two-dimensional space in the case where the wavelength is narrowed). Note that a case where the wavelength range of the G light to be incident on the G ch of the image sensor 48 is narrowed is described in a like manner. In the case where the narrowband G light (the G light of the wavelengths at which a high amount of the G light is absorbed by blood) is used, the difference between the first and second areas is larger than in the case where the broadband G light is used (the second to fifth areas shift in the horizontal axis direction in the case where the wavelength range is narrowed).

In the above description, the wavelength range of one of the B light to be incident on the B ch of the image sensor 48 and the G light to be incident on the G ch of the image sensor 48 is narrowed. Note that the wavelength ranges of both the B light and the G light may be narrowed instead. In this case, as a result of narrowing the wavelength ranges, the second to fifth areas shift in the vertical axis direction and the horizontal axis direction in the two-dimensional space. However, the amount of the shift in the vertical axis direction is smaller than in the case where only the wavelength range of the B light to be incident on the B ch of the image sensor 48 is narrowed. This is because both the absorption coefficient for the B ch and the absorption coefficient for the G ch are increased by the narrowband B light and the narrowband G light. Therefore the difference between the reflection density of the B ch and the reflection density of the G ch is smaller than in the case where only the wavelength range for the B ch is narrowed.

In the above embodiment, the polar coordinate conversion is performed on the first and second signal ratios. The radial coordinate difference or the angular coordinate difference between the first area average value that has been subjected to the polar coordinate conversion and the signal value in each of the second to fifth areas that has been subjected to the polar coordinate conversion is expanded. Thereby the difference in color between the normal mucosal region and the abnormal region is enhanced. Another coordinate conversion method and another color difference enhancement method may be used to enhance the difference in color between the normal mucosal region and the abnormal region. Note that, in the case where the enhanced image is produced by using the color difference enhancement method for expanding the radial coordinate difference or the angular coordinate difference in the polar coordinate system as described in the above embodiment, the color of the normal mucosal region in the enhanced image is the same as that of the normal mucosal region in the normal light image, so that the enhanced image looks natural. The colors of the atrophic mucosal region and the deep blood vessel region in the enhanced image are the same as the actual colors of the atrophic mucosa with the atrophic gastritis and the blood vessels seen through the atrophic mucosa, so that a method similar to the currently used method (for example, ABC screening) may be used for diagnosing the atrophic gastritis.

In the above embodiment, the first area average value is used to enhance the color difference between the normal mucosal region and the abnormal region. Note that the average value of the pixel values of the entire image signal may be used instead. In this case, although the color of the atrophic mucosa and the color of the deep blood vessels may vary on an image-by-image basis, there is a merit that a slight difference between the normal mucosal region and the abnormal region is expanded in accordance with the distribution of each region in the image.

In the above embodiment, the first and second signal ratios are subjected to the polar coordinate conversion. The expansion process for expanding the radial coordinate difference or the angular coordinate difference is performed on the signal that has been subjected to the polar coordinate conversion. Note that the polar coordinate conversion process and the expansion process may be performed in advance and the results of the processes may be stored in a LUT (lookup table) for color difference enhancement. In this case, the first and second signal ratios that are considered to be in the second to fifth areas are calculated using the above-described expressions (1) to (6) in advance. The first and second signal ratios in each of the second to fifth areas and the corresponding results of the calculations using the first and second signal ratios are associated with each other and stored in the LUT for color difference enhancement. The first and second signal ratios that are considered to be in the first area are associated with the values identical thereto and stored in the LUT for color difference enhancement. With the use of the LUT for color difference enhancement, the color difference between the normal mucosal region and the abnormal region is enhanced without the polar coordinate conversion process and the expansion process. Thus a processing load is reduced.

In the above embodiment, the color difference enhancer 82 performs the color difference enhancement process for enhancing the color difference between the abnormal region and the normal region. Note that, with the use of the special light including the blue narrowband component (the blue laser beams and the blue violet laser beams), to which the light absorbing material of the mucosa has high absorption properties, the color difference between the normal mucosal region and the abnormal region (the atrophic mucosal region, the deep blood vessel region, the BA region, or the redness region) is enhanced and displayed without the color difference enhancement process, which is performed by the color difference enhancer 82. In a like manner, with the use of light including a green narrowband component (for example, a wavelength component of 540 to 560 nm), to which the light absorbing material of the mucosa has high light absorption properties, the color difference between the normal mucosal region and the abnormal region (the atrophic mucosal region, the deep blood vessel region, the BA region, or the redness region) is enhanced and displayed without the color difference enhancement process performed by the color difference enhancer 82.

Note that, in the first embodiment, the phosphor 44 is provided in the distal portion 24 of the endoscope 12. Instead, the phosphor 44 may be provided in the light source device 14. In this case, it is preferred to provide the phosphor 44 between the light guide 41 and the blue laser 34.

Second Embodiment

Figure 21:
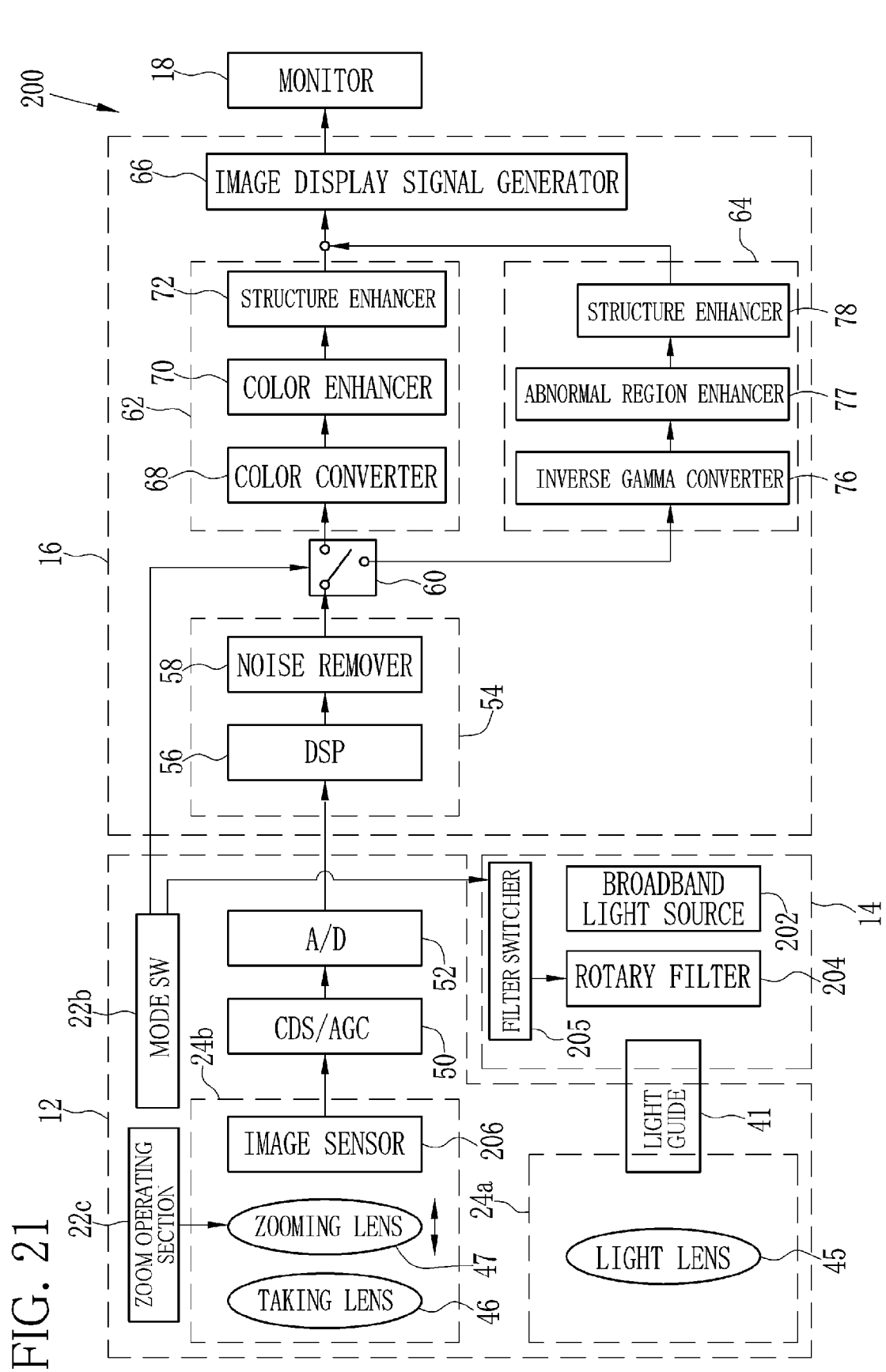
FIG. 21 is a block diagram illustrating functions of an endoscope system of a second embodiment.

In the first embodiment, the RGB image signals are generated simultaneously by the color image sensor. In a second embodiment, the RGB image signals are generated sequentially by a monochrome image sensor. As illustrated in FIG. 21, the light source device 14 of an endoscope system 200 of the second embodiment comprises a broadband light source 202, a rotary filter 204, and a filter switcher 205, instead of the blue laser 34, the blue violet laser 36, and the source controller 40. The illumination optical system 24a of the endoscope 12 eliminates the phosphor 44. The imaging optical system 24b is provided with a monochrome image sensor 206, which eliminates the color filters, in place of the color image sensor 48. Other than those, the endoscope system 200 is similar to the endoscope system 10 of the first embodiment.

The broadband light source 202 comprises a xenon lamp, a white LED, or the like, and emits white light in the wavelength range from blue to red. The rotary filter 204 comprises a normal observation mode filter 208 provided on an inner side and a special observation mode filter 209 provided on an outer side (see FIG. 22). The filter switcher 205 shifts the rotary filter 204 in a radial direction. In a case where the mode is set to the normal observation mode by operating the mode SW 22b, the filter switcher 205 inserts the normal observation mode filter 208 of the rotary filter 204 into the light path of the white light. In a case where the mode is set to the special observation mode, the filter switcher 205 inserts the special observation mode filter 209 of the rotary filter 204 into the light path of the white light.

Figure 22:
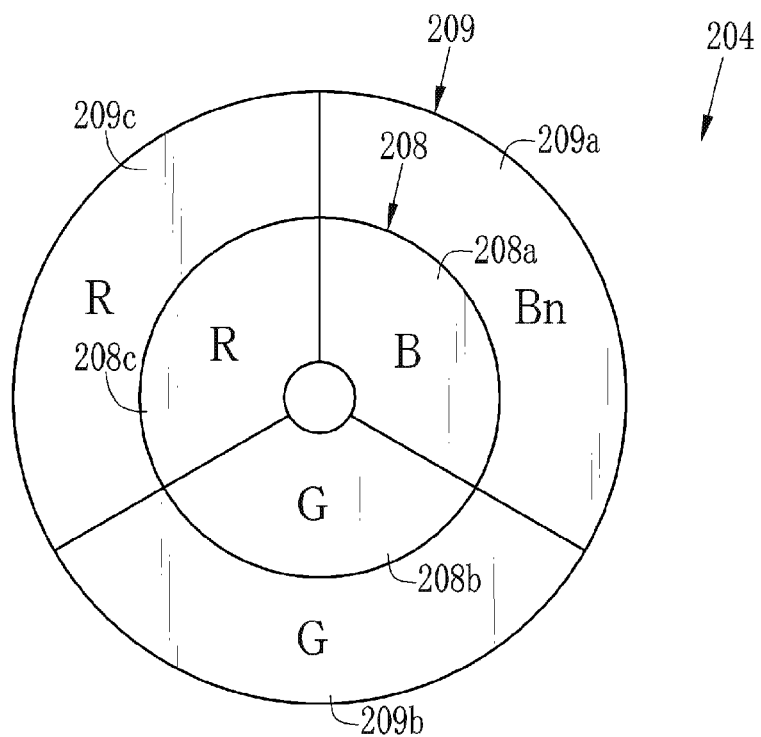
FIG. 22 is a plan view illustrating a rotary filter.

As illustrated in FIG. 22, the normal observation mode filter 208 comprises a B filter 208a, a G filter 208b, and an R filter 208c in a circumferential direction. The B filter 208a transmits blue light of the white light. The G filter 208b transmits green light of the white light. The R filter 208c transmits red light of the white light. In the normal observation mode, the blue light, the green light, and the red light are applied in this order to the object as the rotary filter 204 is rotated.

The special observation mode filter 209 comprises a Bn filter 209a, a G filter 209b, and an R filter 209c in the circumferential direction. The Bn filter 209a transmits blue narrowband light having the center wavelength of 415 nm of the white light. The G filter 209b transmits green light of the white light. The R filter 209c transmits red light of the white light. In the special observation mode, the blue narrowband light, the green light, and the red light are applied in this order to the object as the rotary filter 204 is rotated.

In the normal observation mode, the monochrome image sensor 206 of the endoscope system 200 captures an image of the object every time the blue light, the green light, or the red light is applied to the object. Thereby, image signals of the three colors (RGB) are generated. The normal light image is produced based on the RGB image signals by a method similar to that in the first embodiment.

In the special observation mode, the monochrome image sensor 206 captures an image of the object every time the blue narrowband light, the green light, or the red light is applied to the object. Thereby, a Bn image signal, a G image signal, and an R image signal are generated. The special light image is produced based on the Bn image signal, the G image signal, and the R image signal. The Bn image signal is used in place of the B image signal to produce the special light image. Other than that, the special light image is produced by a method similar to that of the first embodiment.

Third Embodiment

The endoscope system 10 of the first embodiment uses the B image signal, being the narrowband signal containing narrowband wavelength information of the blue laser beams and the blue violet laser beams, to produce the special light image. The endoscope system 200 of the second embodiment uses the Bn image signal, being the narrowband signal containing the narrowband wavelength information of the blue narrowband light, to produce the special light image. In a third embodiment, a blue narrowband image signal is generated by spectral calculation based on a broadband image such as a white light image. Based on the blue narrowband image signal, the special light image is produced.

Figure 23:
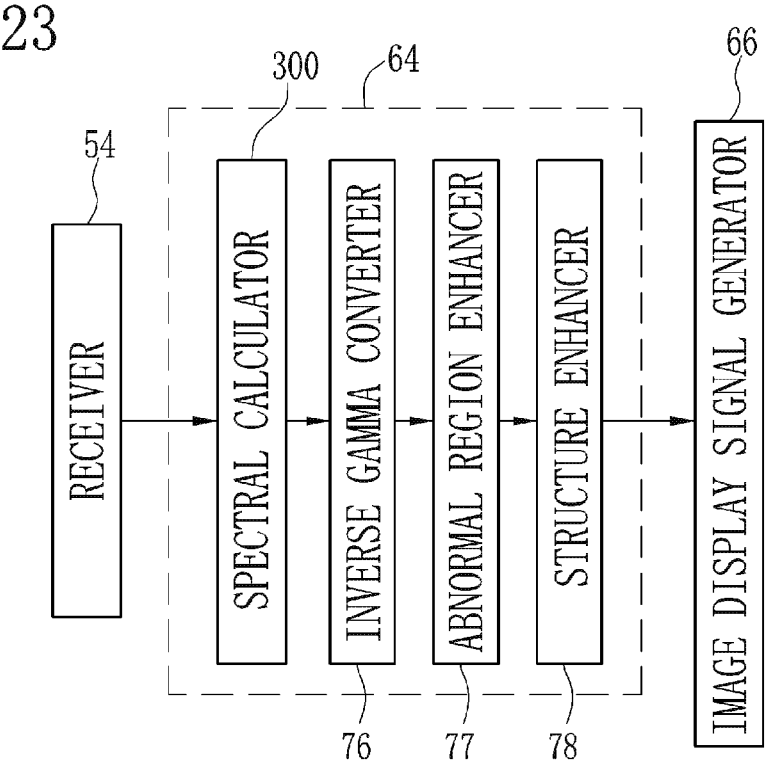
FIG. 23 is a block diagram illustrating functions of a special light image processor of a third embodiment.

In the special observation mode of the synchronization-type endoscope system 10 in the third embodiment, white light, being the broadband light, is emitted instead of the special light. As illustrated in FIG. 23, a spectral calculator 300, which is disposed between the receiver 54 and the inverse gamma converter 76, performs a spectral calculation process based on the RGB image signals generated by imaging the object irradiated with the white light. Thereby the blue narrowband image signal is generated. The spectral calculation method described in Japanese Unexamined Patent Application Publication No. 2003-093336 is used. The special light image is generated, in a manner similar to the first embodiment, based on the blue narrowband image signal generated by the spectral calculator 300, the G image signal, and the R image signal. Note that the white light obtained using the phosphor 44, the broadband light emitted from a broadband light source such as the xenon lamp, or the like may be used as the white light.

The above embodiments describe an example in which the color of the mucosa is faded due to the atrophic gastritis and an example in which the deep blood vessels located beneath the atrophic mucosa are seen through the atrophic mucosa. Note that the color of the mucosa may be faded due to a lesion of another site (for example, a lesion in esophagus or a lesion in large intestine). The present invention also enables enhancing the color difference between the normal region and mucosa, other than the above-described atrophic mucosa, showing fading of color. The present invention also enables enhancing and displaying the deep blood vessels located beneath and seen through the mucosa, other than the atrophic mucosa, showing fading of color.

Note that the above-described first to fourth expansion processes increase the color difference between the abnormal region (the atrophic mucosa, the deep blood vessels, the BA, or the redness) and the normal mucosa while the color of the normal mucosa is maintained unchanged. According to the above embodiments, an image in which the color of the normal mucosa is maintained unchanged is displayed after any of the first, second, third, and fourth expansion processes.

It is necessary to perform the first, second, third, or fourth expansion process as follows to display the image in which the color of the normal mucosa is maintained unchanged as described above. For example, in the first expansion process, the third expansion process, and the fourth expansion process, in which a radial coordinate is expanded, the radial coordinate r that is within the first area is converted into the radial coordinate Er that is equivalent to the radial coordinate r (identical transformation) (see FIG. 26) in a case where the first area is defined to be in a range from "rm−$\Delta$r1" to "rm+$\Delta$r2" (see FIG. 24). For example, the radial coordinate Eris "rm" in a case where the radial coordinate r is "rm". After the first, third, or fourth expansion process, the color of the normal mucosa is maintained unchanged in the image by the identical transformation of the radial coordinate r that is located in the first area.

Figure 24:
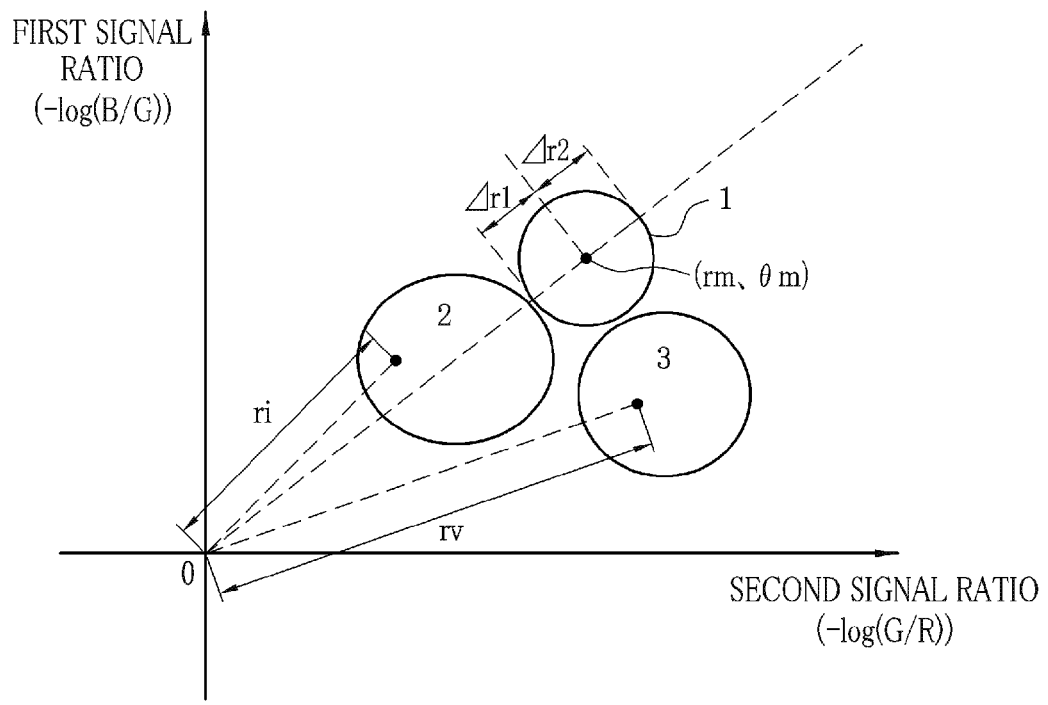
FIG. 24 is an explanatory view illustrating a radial coordinate of the first area, a radial coordinate of the second area, and a radial coordinate of the third area.
Figure 25:
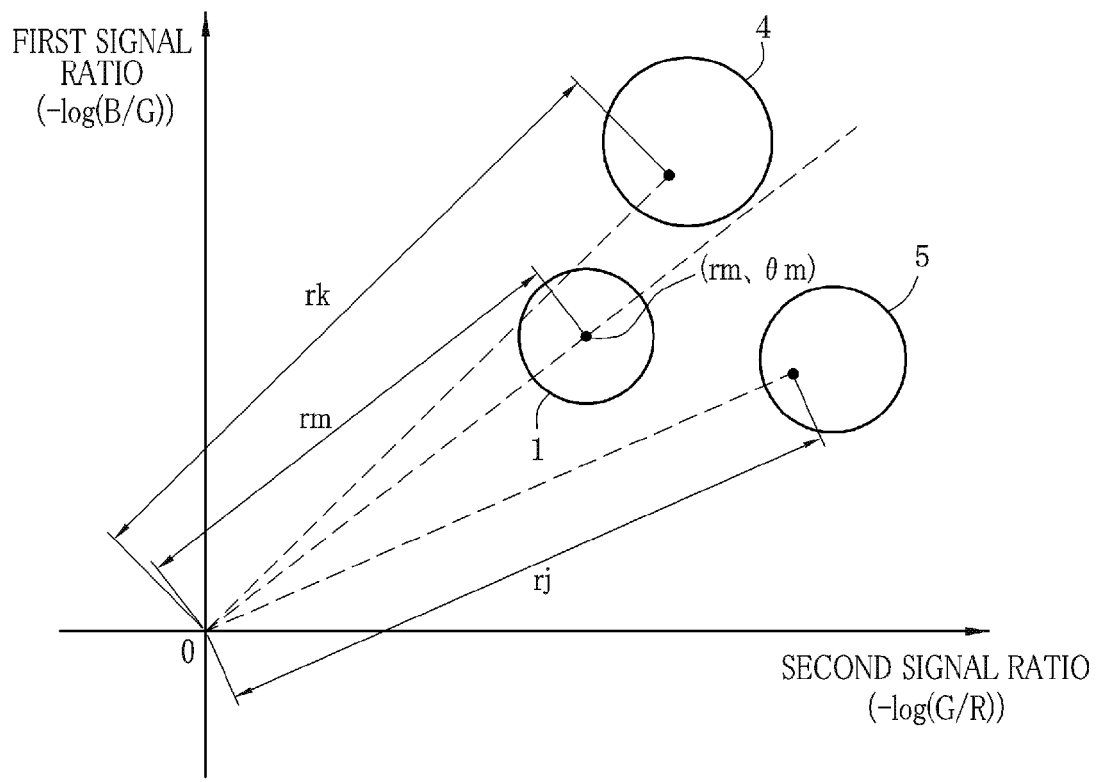
FIG. 25 is an explanatory view illustrating a radial coordinate of the first area, a radial coordinate of the fourth area, and a radial coordinate of the fifth area.
Figure 26:
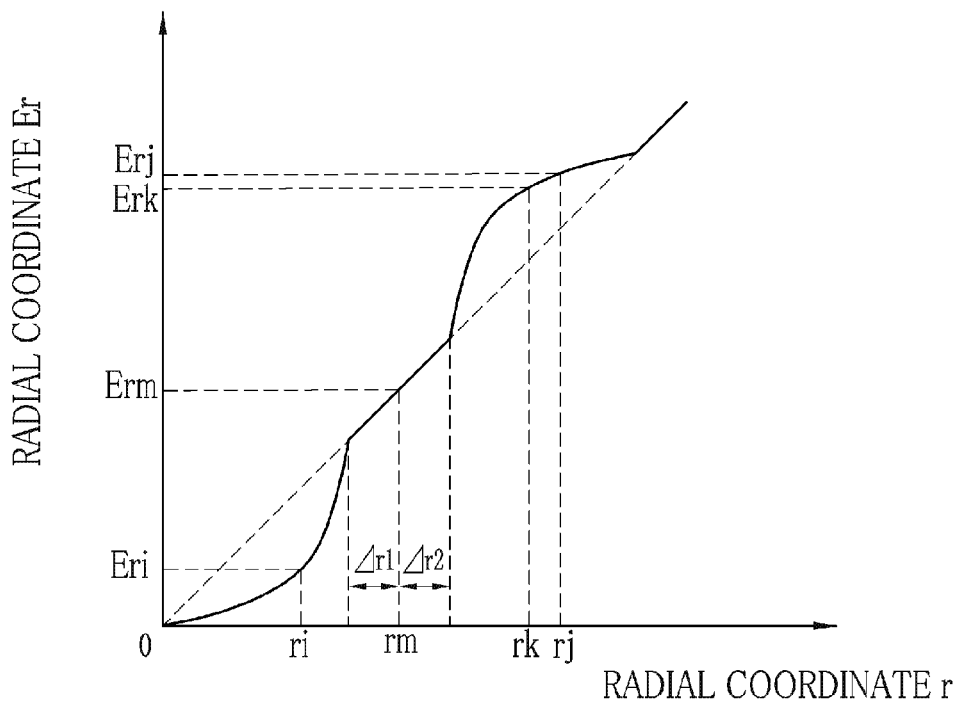
FIG. 26 is a graph illustrating a relationship between radial coordinate r and radial coordinate Er.

As illustrated in FIG. 24, the radial coordinate ri (of the second area) smaller than the first area average value rm is converted into the radial coordinate Eri smaller than the radial coordinate ri (see FIG. 26). As illustrated in FIG. 25, the radial coordinates rk and rj (of the fourth and fifth areas), which are greater than the first area average value rm in most cases, are converted into the radial coordinates Erk and Erj, which are greater than the radial coordinates rk and rj. FIG. 26 illustrates the correspondence between the radial coordinate r and the radial coordinate Er within an angular coordinate $\theta$ of a predetermined range that includes the first to fifth areas. Note that a different correspondence may be set for each angular coordinate $\theta$.

Figure 27:
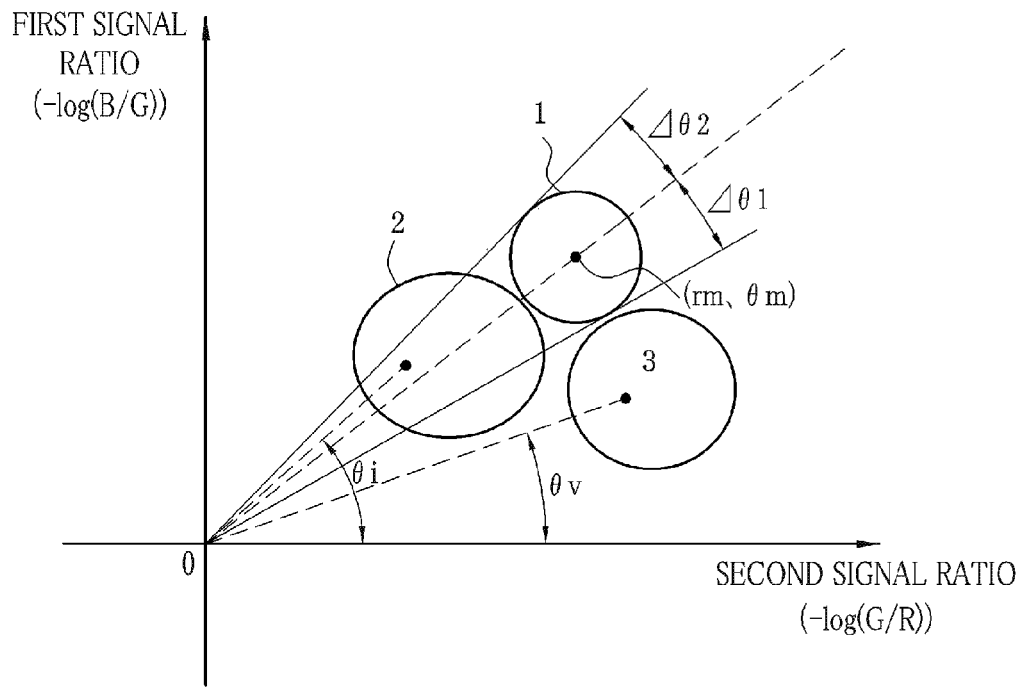
FIG. 27 is an explanatory view illustrating an angular coordinate of the first area, an angular coordinate of the second area, and an angular coordinate of the third area.

In the second expansion process, the third expansion process, and the fourth expansion process, in which the angular coordinate is expanded, the angular coordinate $\theta$ that is within the first area is converted into the angular coordinate E$\theta$ that is equivalent to the angular coordinate $\theta$ (identical transformation) (see FIG. 29) in a case where the first area is defined to be in a range from "$\theta$m−$\Delta\theta$1" to "$\theta$m+$\Delta\theta$2" (see FIG. 27). For example, the angular coordinate E$\theta$ is "$\theta$m" in a case where the angular coordinate $\theta$ is "$\theta$m". Thus, after the second, third, or fourth expansion process, the color of the normal mucosa is maintained unchanged in the image by the identical transformation of the angular coordinate $\theta$ that is located in the first area.

Figure 28:
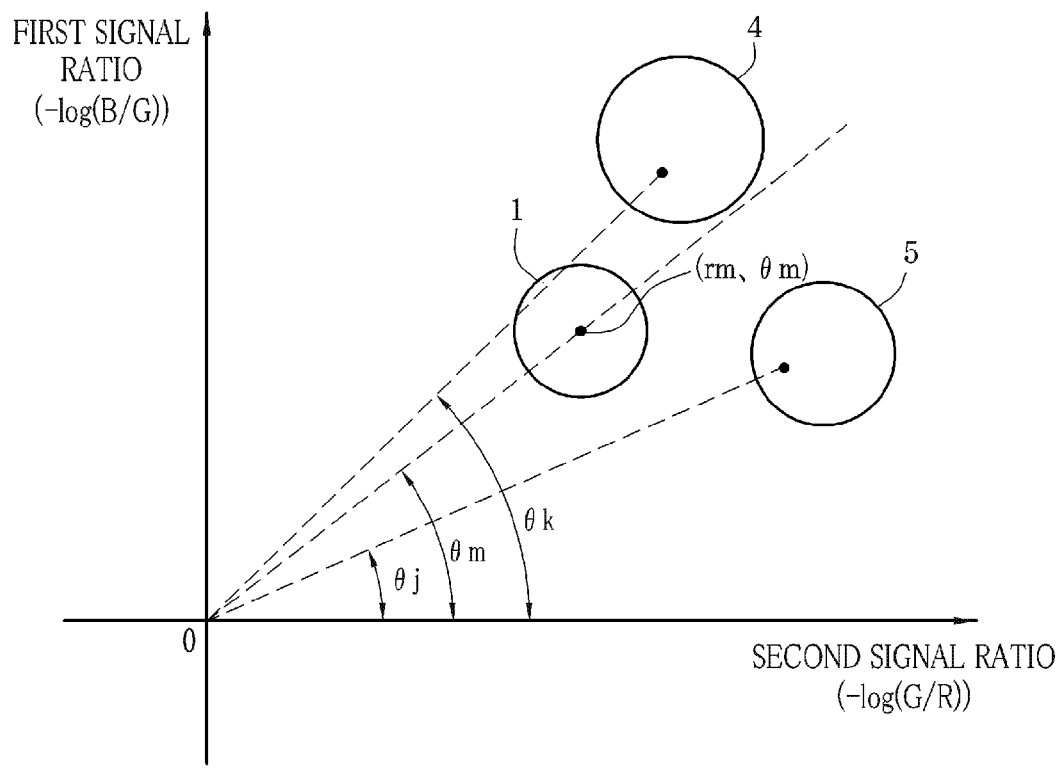
FIG. 28 is an explanatory view illustrating an angular coordinate of the first area, an angular coordinate of the fourth area, and an angular coordinate of the fifth area.
Figure 29:
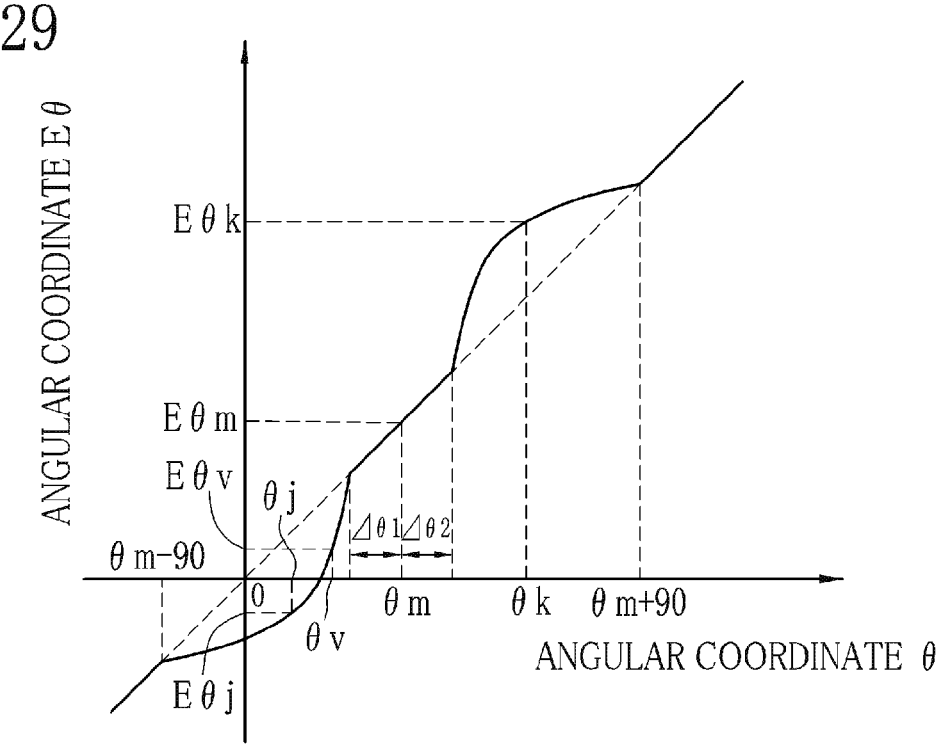
FIG. 29 is a graph illustrating a relationship between the angular coordinate θ and the angular coordinate Eθ.

As illustrated in FIG. 27, the angular coordinate $\theta$v (of the third area) smaller than the first area average value $\theta$m is converted into the angular coordinate E$\theta$v smaller than the angular coordinate $\theta$v (see FIG. 29). As illustrated in FIG. 28, the angular coordinate $\theta$k (of the fourth area), which is greater than the first area average value $\theta$m in most cases, is converted into the angular coordinate E$\theta$k, which is greater than the angular coordinate $\theta$k (see FIG. 29). As illustrated in FIG. 28, the angular coordinate $\theta$j (of the fifth area), which is smaller than the first area average value $\theta$m in most cases, is converted into the angular coordinate E$\theta$j, which is smaller than the angular coordinate $\theta$j (see FIG. 29). Note that, in FIG. 29, "$\theta$m" denotes an angle defined to be within a range from 0° to 90°. "$\theta$m−90" denotes a negative angle. "$\theta$m+90" denotes a positive angle. An angle increases toward the right on the horizontal axis. The angle increases toward the upper end of the vertical axis.

In the above embodiments, the implementation of the present invention is performed during the diagnosis using the endoscope, but not limited thereto. Note that the implementation of the present invention may be performed after the diagnostic endoscopy, based on an endoscopic image stored in a storage unit of the endoscope system. The implementation of the present invention may be performed based on a capsule-endoscopic image captured with a capsule endoscope.

Various changes and modifications are possible in the present invention and may be understood to be within the present invention.

What is claimed is:

1. A method for operating an endoscope system comprising the steps of:
    inputting image signals of three colors including at least one narrowband image signal, with an image signal inputting unit;
    calculating a first signal ratio between the image signals of predetermined two colors and a second signal ratio between the image signals of two colors different from the first signal ratio, based on the image signals of three colors with a signal ratio calculator;
    performing an expansion process with a color difference enhancer, the expansion process expanding a difference between first and second signal ratios in a first area and first and second signal ratios in a specific area different from the first area; and displaying a color difference between normal mucosa and an abnormal region on an object of interest greater than a color difference in a case where all of the image signals of three colors are broadband image signals at the time a display unit displays an image in which the color difference between the normal mucosa and the abnormal region on the object of interest is enhanced based on the first and second signal ratios subjected to the expansion process.

2. An image processing device comprising:
an image signal receiver that receives image signals of three colors including at least one narrowband image signal;
a processing circuitry configured for:
calculating a first signal ratio between the image signals of predetermined two colors and a second signal ratio between the image signals of two colors different from the first signal ratio, based on the image signals of three colors; and
performing an expansion process, the expansion process expanding a difference between first and second signal ratios in a first area and first and second signal ratios in a specific area different from the first area; and
a display that displays an image in which a color difference between normal mucosa and an abnormal region on an object of interest is enhanced based on the first and second signal ratios subjected to the expansion process, the color difference being displayed greater than a color difference in a case where all of the image signals of three colors are broadband image signals.

3. The image processing device according to claim 2, wherein a difference in reflection density between the normal mucosa and the abnormal region is greater than a difference in reflection density in the case where all of the image signals of three colors are the broadband image signals.

4. The image processing device according to claim 3, wherein the difference in reflection density between the normal mucosa and the abnormal region increases as wavelengths corresponding to the narrowband image signal become shorter.

5. The image processing device according to claim 2, wherein the abnormal region includes at least one of mucosa showing fading of color including atrophic mucosa, a blood vessel region beneath the mucosa showing fading of color, a BA (brownish area) region, and a mild redness region.

6. The image processing device according to claim 2, wherein the narrowband image signal is obtained by imaging the object irradiated with narrowband light that is highly absorbed by blood.

7. The image processing device according to claim 6, wherein the narrowband image signal is a blue narrowband image signal obtained by imaging the object irradiated with blue narrowband light that is highly absorbed by the blood or a green narrowband image signal obtained by imaging the object irradiated with green narrowband light that is highly absorbed by the blood.

8. The image processing device according to claim 2, wherein the expansion process is a process for expanding a radial coordinate difference or an angular coordinate difference between the first and second signal ratios in the first area and the first and second signal ratios in the specific area.

9. The image processing device according to claim 2, wherein the expansion process expands the difference between the first and second signal ratios in the first area and the first and second signal ratios in the specific area while the first and second signal ratios in the first area are maintained unchanged, and
the display unit displays an image in which a color of the normal mucosa is maintained unchanged.

10. The image processing device according to claim 2, the processing circuitry further calculating an average value of the first and second signal ratios in the first area, wherein the processing circuitry expands a difference between the average value and the first and second signal ratios in the specific area.

11. The image processing device according to claim 2, wherein a suppression process for reducing the enhancement of the color difference is performed in a high luminance area or a low luminance area in the first area and the specific area.

12. The image processing device according to claim 2, wherein the first signal ratio is a B/G ratio between a B image signal, being the narrowband image signal, and a G image signal, and the second signal ratio is a G/R ratio between the G image signal and an R image signal.

* * * * *